(12) United States Patent
Samadpour

(10) Patent No.: US 8,956,826 B2
(45) Date of Patent: Feb. 17, 2015

(54) TREND ANALYSIS AND STATISTICAL PROCESS CONTROL USING MULTITARGETED SCREENING ASSAYS

(75) Inventor: Mansour Samadpour, Seattle, WA (US)

(73) Assignee: Institute for Environmental Health, Inc., Lake Forest Park, WA (US)

(*) Notice: Subject to any disclaimer, the term of this patent is extended or adjusted under 35 U.S.C. 154(b) by 1350 days.

(21) Appl. No.: 11/107,458

(22) Filed: Apr. 15, 2005

(65) Prior Publication Data

US 2006/0115824 A1    Jun. 1, 2006

Related U.S. Application Data

(60) Provisional application No. 60/562,302, filed on Apr. 15, 2004.

(51) Int. Cl.

| | |
|---|---|
| *C12Q 1/68* | (2006.01) |
| *C12Q 1/02* | (2006.01) |
| *C12Q 1/04* | (2006.01) |
| *C12Q 1/06* | (2006.01) |
| *C12Q 1/10* | (2006.01) |
| *C12Q 1/24* | (2006.01) |
| *G01N 33/569* | (2006.01) |
| *C12Q 1/08* | (2006.01) |
| *C12Q 1/70* | (2006.01) |

(52) U.S. Cl.
CPC .. *C12Q 1/06* (2013.01); *C12Q 1/04* (2013.01); *C12Q 1/689* (2013.01); *G01N 33/569* (2013.01)
USPC ............ 435/34; 435/6.12; 435/29; 435/30; 435/38

(58) Field of Classification Search
None
See application file for complete search history.

(56) References Cited

U.S. PATENT DOCUMENTS

| | | | |
|---|---|---|---|
| 5,402,363 | A | 3/1995 | Siebert |
| 7,118,870 | B2 * | 10/2006 | Field et al. ............... 435/6 |
| 7,919,232 | B2 * | 4/2011 | Samadpour ............... 435/4 |
| 2002/0090626 | A1 | 7/2002 | Hyldig-Nielsen |
| 2002/0151700 | A1 | 10/2002 | Farwick et al. |

OTHER PUBLICATIONS

Doyle et al. 1987. Isolation of *Escherichia coli* O157:H7 from Retail Fresh Meats. Applied and Environmental Microbiology, vol. 53, pp. 2394-2396.*
Samadpour et al.1990. Evaluation of DNA Probes for Detection of Shiga-Like-Toxin-Producing *Escherichia coli* in Food and Calf Fecal Samples. Applied and Environmental Microbiology, vol. 56, pp. 1212-1215.*
Padhye et al.1992. *Escherichia coli* O157:H7: Epidemeology, Pathogenesis, and Methods for Detection in Food. Journal of Food Protection, vol. 55, pp. 555-565.*
Millemann et al. 2000. Evaluation of IS200-PCR and Comparison with Other Molecular Markers to Trace *Salmonella enterica* subsp. *enterica* Serotype Typhimurium Bovine Isolates from Farm to Meat. Journal of Clinical Microbiology, vol. 38, pp. 2204-2209.*
http://en.wikipedia.org/wiki/Quotient, Printed Dec. 29, 2008.*
U.S. Appl. No. 60/562,302, filed Apr. 15, 2004, Samadpour.
Acheson, "How Does *Escherichia coli* O157:H7 Testing in Meat Compare with What We Are Seeing Clinically?," Journal of Food Protection, 2000, pp. 819-821, vol. 63.
Baldwin et al., "Detection and Enumeration of Aromatic Oxygenase Genes by Multiplex and Real-Time PCR," Applied and Environmental Microbiology, 2003, pp. 3350-3358, vol. 69.
Barney et al., "Riboprinting and 16S rRNA Gene Sequencing for Identification of Brewery *Pediococcus* Isolates," Applied and Environmental Microbiology, 2001, pp. 553-560, vol. 67.
Behari et al., "pepA, a Gene Mediating pH Regulation of Virulence Genes in *Vibrio cholerae*," Journal of Bacteriology, 2001, pp. 178-188, vol. 183.
Bekal et al., "Rapid Identification of *Escherichia coli* Pathotypes by Virulence Gene Detection with DNA Microarrays," Journal of Clinical Microbiology, 2003, pp. 2113-2125, vol. 41.
Call et al., "Detecting and genotyping *Escherichia coli* O157:H7 using multiplexed PCR and nucleic acid microarrays," International Journal of Food Microbiology, 2001, pp. 71-80, vol. 67.
Carvalho et al., "Molecular Characterization of Invasive and Noninvasive *Campylobacter jejuni* and *Campylocacter coli* Isolates," Journal of Clinical Microbiology, 2001, pp. 1353-1359, vol. 39.
Conner et al., "Differential patterns of acquired virulence genes distinguish *Salmonella* strains," The Proceedings of the National Academy of Sciences, 1998, pp. 4641-4645, vol. 95.
Darwin et al., "Molecular Basis of the Interaction of *Salmonella* with the Intestinal Mucosa," Clinical Microbiology Reviews, 1999, pp. 405-428, vol. 12.
Faruque et al., "Epidemiology, Genetics, and Ecology of Toxigenic *Vibrio cholerae*," Microbiology and Molecular Biology Reviews, 1998, pp. 1301-1314, vol. 62.
Hale, "Genetic Basis of Virulence in *Shigella* Species," Microbiological Reviews, 1991, pp. 206-224, vol. 55.

(Continued)

*Primary Examiner* — Jon P Weber
*Assistant Examiner* — Kailash C Srivastava
(74) *Attorney, Agent, or Firm* — Davis Wright Tremaine LLP

(57) ABSTRACT

Aspects of the present invention provide novel multi-targeted microbiological screening and monitoring methods having substantial utility for monitoring and control of microbial growth and contaminants, microbiological processes, predictive microbiology, and for exposure and risk assessment. Microbial markers shared by both target and index microbes are used in novel methods for microbial monitoring, monitoring of microbial performance potential, trend analysis, and statistical process control (SPC) in processes or systems that are receptive to a plurality of genetically distinct microbes.

21 Claims, 12 Drawing Sheets

(56) References Cited

OTHER PUBLICATIONS

Heller, "Probiotic bacteria in fermented foods: product characteristics and starter organisms," Americal Journal of Clinical Nutrition, 2001 pp. 374S-379S, vol. 73, Supplement.

Hendrickson et al., "Molecular Analysis of *Dehalococcoides* 16S Ribosomal DNA from Chloroethene-Contaminated Sites throughout North America and Europe," Applied and Environmental Microbiology, 2002, pp. 485-495, vol. 68.

Horz et al., "Detection of Methanotroph Diversity on Roots of Submerged Rice Plants by Molecular Retrieval of pmoA, mmoX, mxaF, and 16S rRNA and Ribosomal DNA, Including pmoA-Based Terminal Restriction Fragment Length Polymorphism Profiling," Applied and Environmental Microbiology, 2001, pp. 4177-4185, vol. 67.

Ke et al., "Development of a PCR Assay for Rapid Detection of *Enterococci*," Journal of Clinical Microbiology, 1999, pp. 3497-3503, vol. 37.

McMahon et al, "Polyphosphate Kinase from Activated Sludge Performing Enhanced Biological Phosphorus Removal," Applied and Environmental Microbiology, 2002, pp. 4971-4978, vol. 68.

Mesarch et al., "Development of Catechol 2,3-Dioxygenase-Specific Primers for Monitoring Bioremediation by Competitive Quantitative PCR," Applied and Environmental Microbiology, 2000, pp. 678-683, vol. 66.

Millemann et al., Evaluation of IS200-PCR and Comparison with Other Molecular Markers to Trace *Salmonella enterica* subsp. *enterica* Serotype Typhimurium Bovine Isolates from Farm to Meat, Journal of Clinical Microbiology, 2000, pp. 2204-2209, vol. 38.

Nataro et al., "Diarrheagenic *Escherichia coli*," Clinical Microbiology Reviews, 1998, pp. 142-201, vol. 11.

Porwollik et al., "Characterization of *Salmonella enterica* Subspecies I Genovars by Use of Microarrays," Journal of Bacteriology, 2004, pp. 5883-5898, vol. 186.

Riley et al., "Detection of Variable DNA Repeats in Diverse Eukaryotic Microorganisms by a Single Set of Polymerase Chain Reaction Primers," Journal of Clinical Microbiology, 1991, pp. 2746-2751, vol. 29.

Rivera et al., "Genotypes Associated with Virulence in Environmental Isolates of *Vibrio cholerae*," Applied and Environmental Microbiology, 2001, pp. 2421-2429, vol. 67.

Samadpour et al., "Occurrence of Shiga-Like Toxin-Producing *Escherichia coli* in Retail Fresh Seafood, Beef, Lamb, Pork, and Poultry from Grocery Stores in Seattle, Washington," Applied and Environmental Microbiology, 1994, pp. 1038-1040, vol. 60.

Sharma et al., "Development of a Single-Reaction Multiplex PCR Toxin Typing Assay for *Staphylococcus aureus* Strains," Applied and Environmental Microbiology, 2000, pp. 1347-1353, vol. 66.

Suzuki et al., "Genetic characterization and specific detection of beer-spoilage *Lactobacillus* sp. LA2 and related strains," Journal of Applied Microbiology, 2004, pp. 677-683, vol. 96.

Suzuki et al., "Genetic characterization of non-spoilage variant isolated from Beer-Spoilage *Lactobacillus brevis* ABBC45," Journal of Applied Microbiology, 2004, pp. 946-953, vol. 96.

Suzuki et al., "Genetic marker for differentiating beer-spoilage ability of *Lactobacillus* paracollinoides strains," Journal of Applied Microbiology, 2004, pp. 712-718, vol. 97.

Takahashi et al., "Classification and Identification of Strains of *Lactobacillus brevis* Based on Electrophoretic Characterization of D-Lactate Dehydrogenase: Relationship between D-Lactate Dehydrogenase and Beer-Spoilage Ability," Journal of Bioscience and Bioengineering, 1999, pp. 500-506, vol. 88.

Vankerckhoven et al., "Development of a Multiplex PCR for the Detection of asa1, gelE, cylA, esp, and hyl Genes in *Enterococci* and Survey for Virulence Determinants among European Hospital Isolates of *Enterococcus faecium*," Journal of Clinical Microbiology, 2004, pp. 4473-4479, vol. 42.

Yamasaki et al., "Genetic and Immunochemical Characterization of Thiocyanate-Degrading Bacteria in Lake Water," Applied and Environmental Microbiology, 2002, pp. 942-946, vol. 68.

Boer et al., "Methodology for detection and typing of foodborne microorganisms," International Journal of Food Microbiology, 1999, pp. 119-130, vol. 50.

Osek, "Development of a multiplex PCR approach for the identification of Shiga toxin-producing *Escherichia coli* strains and their major virulence factor genes," Journal of Applied Microbiology, 2003, pp. 1217-1225, vol. 95.

Somer et al., "A PCR Method Based on 16S rRNA Sequence for Simultaneous Detection of the Genus *Listeria* and the Species *Listeria monocytogenes* in Food Products," Journal of Food Protection, 2003, pp. 1658-1665, vol. 66.

Ibekwe et al., Multiplex Fluorogenic Real-Time PCR for Detection and quantification of *Escherichia coli* 0157:H7 in Dairy Wastewater Wetlands, Applied and Environmental Microbiology, 2002, pp. 4853-4862, vol. 68, No. 10.

* cited by examiner

Positive Confirmation

Negative Confirmation

TREND ANALYSIS AND STATISTICAL PROCESS CONTROL USING MULTITARGETED SCREENING ASSAYS

CROSS-REFERENCE TO RELATED APPLICATIONS

The present application claims the benefit of priority to U.S. Provisional Patent Application No. 60/562,302, filed on 15 Apr. 2004, and entitled "USE OF PATHOGEN AND INDICATOR ORGANISM PROFILE DATA FOR STATISTICAL PROCESS CONTROL OF MANUFACTURING PROCESSES AND SANITATION PRACTICES," and which is incorporated by reference herein it its entirety.

FIELD OF THE INVENTION

Aspects of the present invention relate generally to the use of microbial markers shared by both target and index microbes in novel methods for microbial monitoring, monitoring of microbial performance potential, trend analysis, and statistical process control (SPC) in processes or systems that are receptive to a plurality of genetically distinct microbes.

BACKGROUND

Attempts to detect a particular ('target') microbial presence or contamination thereby are divided in the art into two broad groups: (i) direct specific detection of the target microbe by determining a presence or absence status for a presumably 'target microbe-specific' marker or characteristic; and (ii) indirect detection, based on determining a presence or absence status for a presumably 'indicator microbe-specific' marker, which if present is deemed to be indicative of the presence of the target microbe. Such detection schemes, whether direct (target marker) or indirect (indicator microbe marker), have at least two fundamental problems by virtue of being premised on isolated presence/absence tests that yield only an isolated presence/absence signal.

First, a "presence/absence" test is a hypothesis test for which only two possibilities exist with respect to the null hypothesis: either it is true or it is false. In practice, "presence/absence" tests are thus susceptible to two types of errors: type-1 errors (false positives), occurring when the test result is declared positive when the null hypothesis is true (i.e., the condition being tested for does not exist); and type-2 errors (false negatives), occurring when the test result is declared negative when the null hypothesis is false. These errors are the result of non-analytic sampling and analysis errors having a variety of sources including, for example, instances where the test is not sensitive enough to detect a target-specific marker even if present, or where errors are introduced during collecting and/or preparing samples, executing test procedures, or in calculating results. Additionally, a false positive might occur where a presumed 'target microbe-specific' marker is not absolutely specific, but is associated with one or more genetically distinct microbes. Because of Type 1 and 2 errors, therefore, a single test cannot always be regarded as a definitive measure of whether the microbial behavior is present or absent.

Second, prior art detection schemes are not effectively applicable to statistical process control (SPC). SPC is currently applied during the manufacture of many materials, and consists of the systematic monitoring of trends in process control data (e.g., corrective actions are applied to bring a process or system back into control when trends indicate that processes are deviating from desired ranges. SPC conveys distinct economic advantages to a manufacturer. By verifying, for example, that conditions during the manufacturing process fall within a range, SPC helps reassure that the quality of the finished product will be acceptable. Additionally, trend information can be used to initiate corrective actions before product characteristics fall out of acceptable ranges, thereby increasing yields of acceptable finished products.

However, for the majority of samples tested by prior art presence/absence detection schemes, the particular 'target' or 'indicator' microbes are either not present, or are present at undetectable levels, giving rise to numerous isolated negative values that cannot be effectively used in SPC to provide early warning of process failure, exposure and risk assessment, and to facilitate risk based decision making.

For example, manufacturing of food, drinking water, pharmaceuticals and many other materials requires processes and protocols that result in finished goods with low or no microbial burden. Unfortunately, as described above, the ability to apply SPC to microbiological data is often severely limited. A specific case in point relates to the use of generic $E.$ $coli$ 'count' data from carcasses for SPC of the beef manufacturing processes in abattoirs. The USDA Food Safety and Inspection Service has encouraged the use of 'count' data in this manner. Practically, however, many $E.$ $coli$ count data points fall below the limit of detection in clean/semi-clean environments, and it has become evident that SPC cannot be applied when the majority of the data points do not allow identification of trends.

Equally illustrative are the difficulties faced in attempting to apply trend analysis and SPC to $E.$ $coli$ O157:H7 presence/absence test results generated from "hold and release" testing of beef trim products. Application of trend analysis and SPC to such test results for the purpose of directing meaningful pre-emptive and preventative remedial action is highly desirable, because there are severe adverse economic consequences when a positive (pathogen present) test result is obtained. Practically speaking, however, the incidence rate of positive test results may be very low (ca. 1% for $E.$ $coli$ O157:H7 in beef). Again, it has become evident that SPC cannot be applied when the majority of the data points do not provide positive tangible results that would allow for identification of trends.

*Pronounced need in the art.* There is, therefore, a pronounced need in the art for more reliable and robust methods of determining whether a particular target microbe, or associated property thereof, is present, or optimally present, in a process or system that is receptive to a plurality of genetically distinct microbes. There is also a pronounced need in the art for methods for predicting a presence of a target microbe, or target microbe associated condition in such processes or systems, and for identifying trends for SPC applications to processes or systems that are receptive to a plurality of genetically distinct microbes (e.g., manufacturing environments) to help ensure that finished product meets quality and yield objectives with respect to microbial burden or distribution.

There is a pronounced need in the art for methods of determining microbial performance potential in a process or system that is receptive to a plurality of genetically distinct microbes (e.g., bioremediation, fermentation, spoliation). There is a pronounced need in the art for methods of predicting microbial performance potential in such processes or systems.

There is a need, therefore, to extract, derive and/or generate additional data from microbial test methods that is suitable for the application in the context of microbial detection, trend analysis and SPC methodologies.

SUMMARY OF THE INVENTION

Aspects of the present invention provide novel multi-targeted microbiological screening and monitoring methods having substantial utility for monitoring and control of microbial growth and contaminants, microbiological processes, predictive microbiology, and for exposure and risk assessment. Microbial markers shared by both target and index microbes are used in novel methods for microbial monitoring, monitoring of microbial performance potential, trend analysis, and statistical process control (SPC) in processes or systems that are receptive to a plurality of genetically distinct microbes.

Particular aspects of the present invention use the results of multiple independent "presence/absence" tests involving a plurality of target microbe markers, to determine an aggregate index value that represents a more accurate, robust and useful measure of whether a target microbe or target microbe-associated condition or attribute is present or not. Type 1 and 2 errors represent only a small percentage of all results, therefore, the overall effect on the aggregate index value calculation will be incremental.

Particular embodiments provide methods for pathogen and organism profiling, and generating SPC charts for use in any industrial setting or process, or in any system that requires microbiological control of production, or microbial balance. Such applicable processes and systems include, but are not limited to: food production; manufacturing; processing; storage; transportation and distribution; with respect to microbial pathogens—process sanitation, environmental contaminants, and spoilage organisms; with respect to fermentation processes—determining purity of the seed stock and fermentation contaminants; aseptic processing (e.g., food and pharmaceutical; with respect to sterility and environmental control); water treatment (e.g., with respect to microbiological quality of the raw and treated water, and control of the organisms throughout the distribution system); wastewater treatment (e.g., with respect to microbiological quality of the treated wastewater and biosolids, control of the treatment process, control of the aerobic and anaerobic digestors, and assessment of the impact of the discharged wastewater and application of bio-solids on the receiving environments); control of microbial contaminants and assessment of their impact in the indoor environment and indoor air quality assessment studies; environmental microbiology (e.g., with respect to monitoring the microbiological quality of shellfish, shellfish beds and cultured aquatic organisms, assessing the microbiological quality of recreational waters and swimming beaches, assessing the microbiological quality of bodies of water, conducting impact assessment of point and non-point-sources); feed microbiology (e.g., in determining the microbiological quality and safety of the feed); soil microbiology (e.g., in assessing the overall microbiology and population structure of soil organisms, in assessing target organisms that can indicate environmental contamination or organic and inorganic reservoirs (e.g., oil fields)).

DETAILED DESCRIPTION OF THE INVENTION

Figure 1:
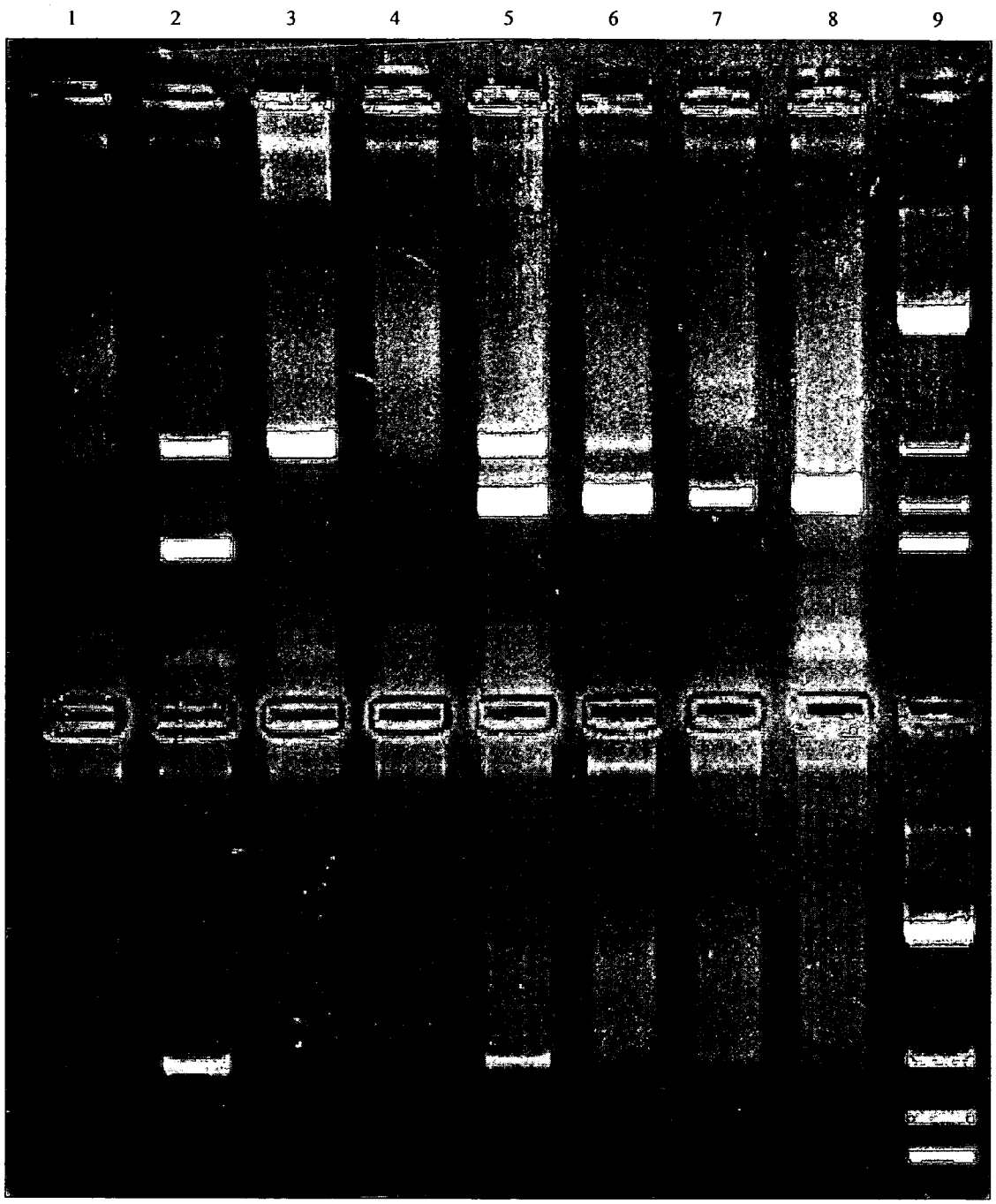
FIG. 1 shows, according to EXAMPLE 1 herein, exemplary results for a 4-band multiplex PCR test for *E. coli* O157:H7. In the Figure test results are shown as two rows of 9 "lanes" in which genetic targets amplified by polymerase chain reaction (PCR) techniques have been separated by agarose gel electrophoresis and visualized using ethidium bromide dye in a UV transilluminator. Positive controls with four bands each are shown in the right hand lanes. Each of the other lanes has bands appearing, indicating the presence of 'index' microbes'; namely, microbes (e.g. organisms) that are also detected by one or more of the *E. coli* O157:H7 markers. Note that in this example, none of the lanes shows the presence of all four bands required to indicate a positive result for the presence of *E. coli* O157:H7.

In prior art microbial detection schemes, samples are tested by conventional presence/absence detection schemes, and the particular 'target' or 'indicator' microbes are either not present, or are present at undetectable levels giving rise to independent, primarily negative values that cannot be effectively used in monitoring to establish trends or to enable statistical process control (SPC) applications to provide early warning of process failure, exposure and risk assessment, and risk based decision making. Additionally, independent prior art presence/absence tests for particular target microbes, or for target microbe-associated conditions or attributes, either cannot or should not be regarded as a definitive measure of whether a particular 'target' microbe, or 'target' microbe-associated condition or attribute, is present or absent. This is because, as discussed above (under "Background"), conventional presence/absence test schemes are susceptible to both type-1 (false positives) and type-2 (false negative) errors.

These and other problems relating to microbial monitoring are solved by aspects of the present invention that use microbial markers shared by both target and index microbes in novel methods for microbial monitoring, monitoring of microbial performance potential, trend analysis, and statistical process control (SPC). The inventive methods allow, inter alia, for control of microbial growth, contaminant and management of microbiological processes, predictive microbiology, and for exposure and risk assessment.

Particular embodiments provide novel test methods in which the outcome (herein referred to as an "index value") of a plurality of presence/absence tests for a corresponding plurality of particular target microbe markers is based upon an aggregate analysis scheme applied to the isolated presence/absence marker test values. The individual presence/absence marker test values each correspond to a specific property or attribute of a target microbe being screened for, and according to the present invention, while the target microbe is considered present only when at least a plurality (and preferably at least a majority) of the markers tested are determined to be present, the inventive aggregate analyses provide for determination of useful index values even where the sum of the markers present is not great enough to indicate the presence of the target microbe or the target microbe-associated condition or attribute.

The inventive utility of the index value is premised on the fact that at least one of the target microbe markers also detects one or more index microbes (or index-microbe-associated condition or attribute) present in the test sample. Such index microbes are genetically distinct microbes, and are typically from sources in common with the target microbe, or typically behave in a fashion similar to the target microbe or organism when, for example, microbial interventions are applied or when favorable growth conditions are encountered. When such index organisms are present, they give rise to positive signals for a subset of the target microbe markers, and according to the present invention, while a sufficient number of such positive signals can support a conclusion that the target microbe is present, a lesser number (or even one such marker) also has substantial utility in providing index values that are predictive of, or indicative of the likelihood of whether the target microbe or target microbe-associated condition or attribute will be detected.

Therefore, aspects of the present invention, in contrast to prior art methods, extract and use additional data from microbial test methods in that index microbes (or index-microbe-associated condition or attribute) are detected, and an index value is calculated even in instances where the target microbe of interest is deemed to be "absent," based on the aggregate test results. Preferably, a mathematical index value is calculated, based on the number of markers for which positive results are obtained compared to the total number of possible positive marker results.

Preferably, this index value is tracked over time, and/or among different sample source locations within a process or system, and by applying trend analysis, changes in the index value that reflect the probability that the target microbe, or target microbe-associated condition or attribute will be detected can be tracked. When the trend indicates an increased probability, there is an opportunity through the application of process control (e.g., SPC) to take meaningful pre-emptive and/or remedial actions relating to the target microbe, or to the target microbe-associated conditions or attributes.

Particular aspects comprise use of an aggregate of presence/absence signals that are either generated by application of separate test methods, or by using one or more multi-plex test methods, or a combination of such individual or multiplex methods to monitor target microbes (e.g., pathogens), a class of target microbe (e.g., pathogenic), or a target microbe-associated condition or attribute. Preferably, the analysis is applied to enriched samples, initially collected from a process or system (e.g., manufacturing environment including final product, incomplete product from intermediate process steps, raw ingredients, treatment materials, equipment swabs, and environmental samples). Preferably, samples are enriched for the target microbe or appropriate taxon thereof. Such enrichment increases detection by, and enhances utility of the test methods, because of sensitivity considerations and increases the number of applicable possible test methods. Additionally, some tests result in several signals (e.g., multiplex PCR), thus many test results are available which may form the basis for SPC according to preferred embodiments of the present invention.

In particular embodiments, the presence/absence microbial test methods include, but are not limited to multiplex PCR reaction(s), DNA chips, dot blots, multi- and single-target lateral flow devices, and combinations thereof. Preferably, the methods comprise determination of presence/absence microbial tests for detection of microbe markers including, but not limited to ribosomal RNA genes (including those for particular taxons of microbes or organisms), virulence factors or putative virulence factors found in target microbes, gene segments which are found in target and/or index microbes, or in taxons thereof, metabolic products (e.g., including by-products) associated with microbial taxons, and antigens which are associated with target and/or index microbes, or with taxons thereof.

Preferably, the assay suitable for detection of pathogenic or microbial contamination is selected from the assay group consisting of immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophage-detection-based assays, classical microbiology-based assays, and chemical or biochemical assays based on the detection of compounds associated with particular target organisms or groups of target organisms, and combinations thereof.

Preferably, the microbe or pathogen is selected from the group consisting of *Escherichia coli* O157:H7 (*E. coli* O157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella, Listeria, Yersinis, Campylobacter, Clostridial species, Staphylococcus* spp.; frank and opportunistic bacterial, fungal, viral, parsitic pathogens; indicator organisms including heterotrophes, generic *E. coli*, total and fecal coliforms and enterococcus; spoilage organisms including Pseudomonas; indicator molecules including glial fibrillary acid protein (GFAP), transmissable spongiform encephalopathy (TSE) agents (prions), including bovine spongiform encephalopathy (BSE) agents, scrapie, chronic wasting disease; and combinations thereof. Additional microbe sor pathogensare selected from the group consisting of *Staph. aureus, Bacillus cereus*, and *Clostridium botulinum, Clostridium perfringes, Vibrio cholerae* and *V. parahemolyticus, Yersinia enterocolitica, Yersinia pestis, Brucella. Francisella, Aeromonas* and *Plesiomonas, Citrobacter, Enterobacter, Klebsiella, Morganella, Proteus, Providencia, Serratia*, and *Shigella*.

Preferably, the pathogen or microbe is *Escherichia coli* O157:H7 (*E. coli* O157:H7).

In particular embodiments, a point system is applied to the test signals, wherein each signal is assigned one or more points if a positive result is observed, and an index value is calculated based on the ratio of the number of points observed to the collective total number of possible points. In more specific aspects, the test methods comprise a combination of a multiplex (e.g., 4-band)-PCR test and a lateral flow device test (e.g., for detecting antigen by ELISA) for the detection of a target microbe (e.g., *E. coli* O157:H7) and an index value (e.g., 'sanitation index') is calculated as a $\% = 100 \times TS/(5 \times T)$ (see herein below for variable definition).

In preferred aspects, the index value is plotted over time, or is compared among samples of differing source within a process or system, and temporal or spatial changes in the index values are analyzed to identify trends. Preferably, identified trends relating to changes in index value are used in making process control decisions (e.g., consistent with the principles of art recognized SPC).

Specific Embodiments

Aspects of the present invention provide a method for microbial monitoring in a process or system, comprising: a) obtaining, at each of a plurality of time points, at least one test sample from a process or system receptive to a plurality of genetically distinct microbes; b) determining for each test sample, and by using a plurality of suitable tests, a presence or absence for each of a plurality of markers of at least one target microbe, wherein at least one of the markers also detects at least one index microbe present in the sample, and wherein the at least one target microbe is considered present only when at least a plurality of all markers tested is determined to be present; and c) further determining, for each time point, at least one index value that is proportional to the number of markers present, whereby temporal changes in the index value are monitored, and microbial monitoring in a process or system is, at least in part, afforded.

Preferably, the method further comprises the use of the index values determined in c) for purposes of trend analysis to assess a status associated with the process or system. Preferably, the method further comprises the use of the index values determined in c) for purposes of intervention or control of the process or system.

Preferably, the index microbe is a microbe that is genetically distinct from the at least one target microbe, but is otherwise correlatable with the target microbe by virtue of at least one common property selected from the group consisting of: coordinate source association; coordinate growth condition response; indicator organism relationship; same family taxon; same genus taxon; same species taxon; same biotype; same serotype; same virulence group; common functional genes; common virulence factors; common enzymes and enzymatic pathway(s); common engineered genes or traits; common metabolites or by-products; coordinate sensitivity to antimicrobial agents or conditions, and same strain attribution.

Preferably, the samples are enriched prior to determining in b).

Preferably, the index values determined in c) are calculated by a formula suitable to allow for correlating the number of observed marker presence events and normalizing them over the number of samples taken. Preferably, the index values determined in c) are proportional to the quotient of the number of markers present divided by the total number of markers. Preferably, the determining the index value in c) further comprises weighting, for purposes of calculating the index value, the value of the presence of at least one of the markers relative to another. Preferably, the weighting is based on at least one common property between target and index microbes, wherein the index microbe is a microbe that is genetically distinct from the at least one target microbe, but is otherwise correlatable with the target microbe by virtue of at least one common property selected from the group consisting of: coordinate source association; coordinate growth condition response; indicator organism relationship; same family taxon; same genus taxon; same species taxon; same biotype; same serotype; same virulence group; common functional genes; common virulence factors; common enzymes and enzymatic pathway(s); common engineered genes or traits; common metabolites or by-products; coordinate sensitivity to antimicrobial agents or conditions, and same strain attribution.

Preferably, the at least one target microbe is considered present when a specific marker profile is determined to be present. Preferably, the at least one target microbe is considered present when at least a majority of all markers tested are determined to be present in a particular sample.

Preferably, the methods further comprise establishment of at least one threshold index value that is predictive of the presence of the target microbe in the process or system. Preferably, the at least one threshold index value is an upper confidence limit, as defined herein, that is proportional to the standard deviation of the index values over an investigated time range. Preferably, the at least one threshold index value corresponds to a particular process interval selected from the group consisting of daily, weekly, monthly, seasonal, and process phase based intervals, and is predictive of a status of the process or system.

Preferably, the markers are selected from the group consisting of genetic markers, antigenic markers, metabolite and metabolite by-product markers, and combinations thereof. Preferably, the markers are selected from the group consisting of DNA markers, virulence factor genes, virulence factors or putative virulence factors, toxins, enzymes, proteins, macromolecules, metabolic byproducts, surface antigens, adhesion proteins, ribosomal gene markers, and combinations thereof. Preferably, the number of markers tested is at least 5. Preferably, at least one marker comprises an antigen of a surface antigen protein of the target microbe, and at least 4 markers correspond to genetic markers of the target organism.

In particular embodiments, the time points are separated by a period selected from the group consisting of seconds, minutes, hours, days, weeks, months, years and combinations thereof.

Preferably, the at least one target microbe is selected from the group consisting of a pathogens, spoilage organisms, beneficial organisms, bioremedial organisms, indicator organisms, fermentation-related organisms, and combinations thereof. Preferably, the pathogen is characterized by at least one property selected from the group consisting of foodborne, waterborne, airborne, bloodborne, sexually transmitted, vectorborne, and zoonotic organism. Preferably, the pathogen is selected from the group consisting of bacterial, viral, fungal and parasitic microorganisms, and by-products of the preceding. Preferably, the pathogen is selected from the group consisting of pathogenic organisms listed in TABLE 2 herein above. Preferably, the pathogenic organism is *E. coli* O157:H7.

In particular embodiments, the spoilage organism is selected from the group consisting of bacterial, viral, fugal and parasitic microorganisms, and by-products of the preceding. In particular embodiments, the fermentation-related organism is selected from the group consisting of bacterial, viral, fugal and parasitic microorganisms, and by-products of the preceding.

In particular embodiments, the tests are selected from the group consisting of immunoassays, ELISA assays, antigen-antibody based detection methods, ligand-antigen detection methods, nucleic acid amplification-based assays, PCR, multiplex PCR, nucleic acid hybridization-based assays, biosensor assays, immunostaining-microscopy-based assays, nucleic acid-array-based assays, DNA chip-based assays, dot blots, multi- and single-target lateral flow devices, bacteriophage-detection-based assays, microbiology-based assays, and chemical and biochemical assays for detection of compounds, microbial byproducts, metabolites, organic and inorganic molecules associated with the at least one target microbe.

In particular embodiments, the the test sample is a composite sample comprised of a plurality of samples collected from different sources or locations within the process or system.

Additional embodiments of the present invention provide methods for monitoring of microbial performance or potential thereof in a process or system, comprising: a) obtaining, at each of a plurality of time points, at least one test sample from at least one source location of a process or system receptive to a plurality of genetically distinct microbes; b) determining for each test sample, and by using a plurality of suitable tests, a presence or absence for each of a plurality of microbial markers, wherein the markers are selected from the group consisting of genetic markers, antigenic markers, metabolic markers, and combinations thereof; and c) further determining, for each time point, a microbial performance index value that is proportional to the number of markers present, whereby temporal changes in the performance index value are observable, and monitoring of microbial performance or potential thereof in a process or system is, at least in part, afforded.

Preferably, the method comprises use of the microbial performance index value determined in c) for purposes of trend analysis to assess a status associated with the process or system. Preferably, the method comprises use of the microbial performance index value determined in c) for purposes of intervention or control of the process or system.

Preferably, the samples are enriched prior to determining in b).

Preferably, the microbial performance index values determined in c) are calculated by a formula suitable to allow for correlating the number of observed marker presence events and normalizing them over the number of samples taken. Preferably, the microbial performance index values determined in c) are proportional to the quotient of the number of markers present divided by the total number of markers.

Preferably, determining the microbial performance index value in c) further comprises weighting, for purposes of calculating the microbial performance index value, the value of the presence of at least one of the markers relative to another. Preferably, the weighting is based on relevance to a particular aspect of the microbial performance being monitored.

Preferably, the method further comprises establishment of at least one threshold microbial performance index value that is indicative of a level of microbial performance potential of the process or system. Preferably, the at least one threshold microbial performance index value is an upper confidence limit, as defined herein, that is proportional to the standard deviation of the microbial performance index values over an investigated time range. Preferably, the at least one threshold microbial performance index value corresponds to a particular process interval selected from the group consisting of daily, weekly, monthly, seasonal, and process phase based intervals, and is indicative of a status of the process or system. Preferably, the at least one threshold microbial performance index value corresponds to a particular process interval selected from the group consisting of daily, weekly, monthly, seasonal, and process phase based intervals, and is predictive of a status of the process or system.

Preferably, the genetic markers, antigenic markers and metabolic markers are selected from the group consisting of microbial DNA markers, ribosomal gene markers, microbial RNA markers, surface antigens, adhesion proteins, toxins, proteins, plasmid markers, microbial enzyme markers, microbial enzyme activity markers, microbial metabolites and metabolic by-products, and combinations thereof. Preferably, the number of markers tested is at least 5.

In particular embodiments, the time points are separated by a period selected from the group consisting of seconds, minutes, hours, days, weeks, months, years and combinations thereof.

Preferably, the tests are selected from the group consisting of immunoassays, ELISA assays, antigen-antibody based detection methods, ligand-antigen detection methods, nucleic acid amplification-based assays, PCR, multiplex PCR, nucleic acid hybridization-based assays, bio-sensor assays, immunostaining-microscopy-based assays, nucleic acid-array-based assays, DNA chip-based assays, dot blots, multi- and single-target lateral flow devices, bacteriophage-detection-based assays, microbiology-based assays, and chemical and biochemical assays for detection of compounds, microbial byproducts, metabolites, organic and inorganic molecules associated with microbes, and combinations thereof.

Preferably, the microbial performance potential is selected from the group consisting of bioremediation potential, fermentation potential, spoilage potential, pathogenic potential, beneficial organism potential, indicator organism potential, and combinations thereof. Preferably, the microbial performance potential is that of bioremediation potential, and wherein at least two of the markers are selected from the group consisting of aromatic oxygenase genes, catechol 2,3-dioxygenase, nucleic acid marker for *dehalococcoides* group organisms, methanotroph markers, pmoA gene (PmoA) markers, methane monooxygenase (pMMO) markers, *Rhodocyclus*-like beta-*Proteobacteria* markers, phosphate kinase markers, Thiocyanate-Degrading Bacteria markers and combinations thereof.

In particular embodiments, the test sample is a composite sample comprised of a plurality of samples collected from different sources or locations within the process or system.

Applications of Inventive Microbial Monitoring Methods

Generally speaking, the inventive microbial monitoring aspects of the present invention may be applied to any kind of sample obtained from an environment where food, drinking water, pharmaceuticals or any other finished good requiring microbial monitoring and control (e.g., in manufacturing processes or systems requiring low or no microbial burden, or in processes where microbial performance or the potential thereof needs to be monitored). Such samples include, but are not limited to, final product, incomplete product from intermediate process steps, raw ingredients, treatment materials, equipment swabs, and environmental samples.

Accordingly, particular embodiments provide methods for microbial profiling, monitoring, SPC, for use in any industrial setting or process, or in any system that requires microbiological control of production, or microbial balance. Such applicable processes and systems include, but are not limited to: food production (e.g., food manufacturing; processing; storage, transportation and distribution); processes or systems susceptible to microbial pathogens where process sanitation is relevant; environmental systems and processes susceptible to contaminants; systems and processes susceptible to spoliation (spoilage organisms); fermentation processes and systems (e.g., where monitoring the fermentation process, and the purity of the seed stock and fermentation contaminants is important); aseptic processing processes (e.g., with respect to sterility and environmental control of food and pharmaceutical processes); water treatment systems and processes (e.g., with respect to microbiological quality of the raw and treated water, and control of the organisms throughout the distribution system); wastewater treatment (e.g., with respect to microbiological quality of the treated wastewater and bio-solids, control of the treatment process, control of the aerobic and anaerobic digestors, and assessment of the impact of the discharged wastewater and application of bio-solids on the receiving environments); indoor air quality (e.g., with respect to control of microbial contaminants and assessment of their impact in the indoor environment and indoor air quality assessment studies); environmental microbiology (e.g., with respect to monitoring the microbiological quality of shellfish, shellfish beds and cultured aquatic organisms, assessing the microbiological quality of recreational waters and swimming beaches, assessing the microbiological quality of bodies of water, conducting impact assessment of point and non-point-sources); feed microbiology (e.g., in determining the microbiological quality and safety of the feed); soil microbiology (e.g., in assessing the overall microbiology and population structure of soil organisms, in assessing target organisms that can indicate environmental contamination or organic and inorganic reservoirs (e.g., oil fields)); and bioremediation.

EXAMPLE 1

Microbial Monitoring of Processes and Systems Susceptible to *Escherichia coli* O157:H7

This EXAMPLE describes an exemplary application of particular aspects of the inventive microbial monitoring methods to the beef industry.

Regulatory agencies strive to continually improve the safety and the quality of food products and related processes, including, but not limited to, beef products and beef producers. For example, in response to the recent FSIS directives and Guidelines, many beef producers have adopted a sampling plan that involves testing of trim, ground beef or both for the specific microbial pathogen *E. coli* O157:H7 after it has been produced, but before it has been delivered to customers. The sampling plan is a 'hold-and-release' plan which dictates that the trim or ground beef is not released by the producing facility to a customer until negative laboratory results are obtained for the presence of *E. coli* O157:H7. While the majority of abattoirs (slaughterhouses) conduct daily testing of final products for *E. coli* O157:H7. the nature of the data (presence/absence) and the infrequency of positive results make the data unsuitable for applying SPC, as discusses in detail herein above.

Methods; Target Microbe Detection.

The present applicant has developed a detection method for *E. coli* O157:H7 that is now used in about 20% of the "hold and release" testing performed in the United States beef industry. The method is based on a four-band multiplex method, combined with a method comprising an ELISA-based lateral flow device. The four bands of the multiplex method target *E. coli* O157:H7 genes that express: O157 antigen; intimin (adhesion protein); and two shiga-like toxins. The lateral flow device detects the O157 surface antigen protein itself where it is being expressed. According to this multi-target assay, a 'positive' result for *E. coli* O157:H7 is indicated by the appearance of all four bands (markers) associated with respective genes possessed by E. coli O157:H7, or the appearance of any three such bands, along with the distinctive band in the lateral flow device assay. Unless these criteria are met, the sample is declared to be 'negative' for the presence of E. coli O157:H7. However, these genes, or the surface antigen protein, may be shared by other 'index' microbes or organisms (e.g., those with similarities to E. coli O157:H7), so that any of these markers may detect an index microbe that is present in the sample being assayed. Thus, the appearance of any of the five bands in the absence of a definitive positive for E. coli O157:H7, is indicative of the presence of one or more index microbes or organisms.

An example of a multiplex PCR result is shown in FIG. 1. Positive controls with four bands each are shown in the right hand lanes of the figure, which shows a compound gel having two sets of samples; one above the other. Several of the other lanes have one or more bands appearing, indicating organisms that are detected by the respective markers (e.g., that share genes with E. coli O157:H7). In this instance, none of the lanes has all four bands required for indicating a positive result for the presence of E. coli O157:H7. Thus, the figure shows that all field samples in this instance are negative for the presence of E. coli O157:H7, yet bands are appearing from which, according to aspects of the present invention, information can be derived regarding the presence of index organisms (e.g., those sharing genetic similarities with E. coli O157:H7).

The additional information provided by the presence of the index signals is exploited herein. According to aspects of the present invention, organisms with similarities to E. coli O157:H7 act as index organisms (i.e. they are detected by E. coli O157:H7 markers, and thus share properties with E. coli O157:H7 (e.g., genetically similarity, common sources, display coordinate behavior when microbial intervention strategies are applied or when favorable growth conditions are encountered, etc.).

According to this exemplary assay, the appearance of one or more bands (marker signals) in the combination of the 4-band multiplex and the lateral flow device analysis methods is indicative of the presence of one or more index organisms. Significantly, according to the present invention, tracking of such index organisms (or index organism-associated condition or attribute) provides a novel tool for directing meaningful process and system control (e.g., for directing meaningful preemptive and preventative remedial action to control E. coli O157:H7)

Specifically, an aggregate 'index value' (referred to in this particular EXAMPLE as a "Sanitation Index" value) is determined, based on the appearance of bands in the combination of the 4-band multiplex and lateral flow device E. coli O157:H7 analysis methods. Thus, in this particular embodiment, there are five possible index band (marker) signals: four (4) for the multiplex method; and one (1) for the lateral flow device. Where any of the band (marker) signals are observed for a given sample, 1 point is recorded. The maximum score that can be recorded for a given sample is 5, which would correspond to a positive finding for the presence of E. coli O157:H7. In this exemplary implementation, a 'positive' result for E. coli O157:H7 is indicated by the appearance of all four multiplex PCR bands (markers) associated with respective genes possessed by E. coli O157:H7, or the appearance of any three such bands, along with the distinctive band in the lateral flow device assay. Significantly, however, anything with a score greater than 0 (one or more bands appear) but less than that required for a positive result for the presence of E. coli O157:H7, is nonetheless positive for the presence of index microbes (e.g., organisms).

At a typical beef producing facility, anywhere between 25 and 100 hold and release E. coli O157:H7 'Lot' tests are performed daily. For such inventive applications, the results of counting points for individual samples are combined to form a daily Sanitation Index value according to the following formula:

$$\text{Sanitation Index},\% = 100 \times TS/(5 \times T)$$

Where: TS=Total number of positive bands observed for all samples; T=Total number of samples; and 5=Number of bands possible per sample.

The results can, for example, be plotted daily, and over time, the patterns of the Sanitation Index values can be analyzed using basic principles of Statistical Process Control. Such an example is shown in FIG. 2.

Figure 2:
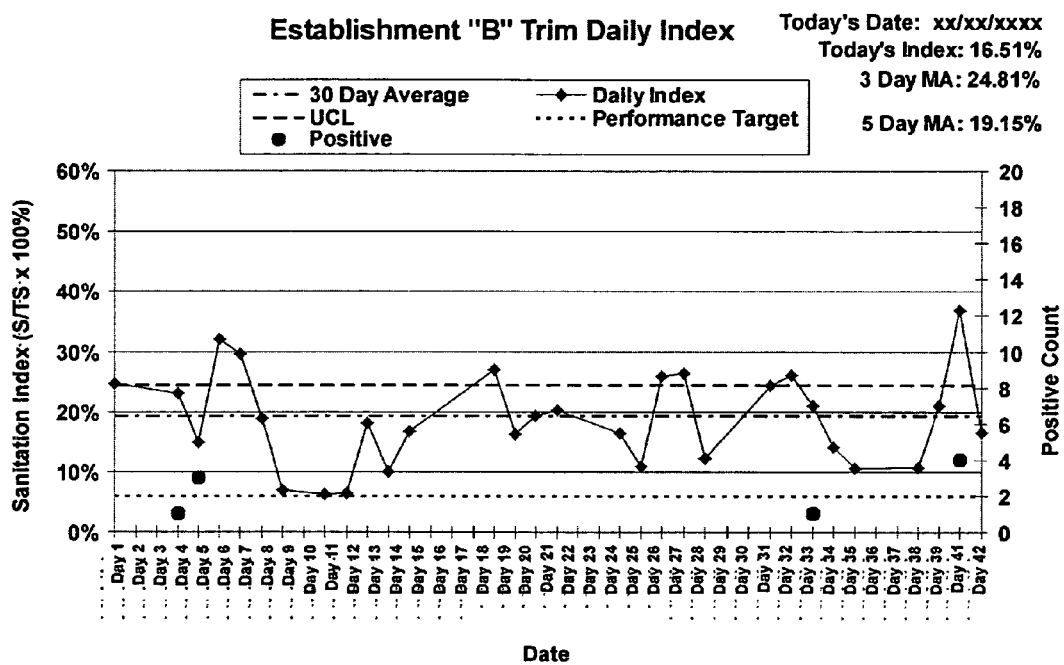
FIG. 2 shows, according to EXAMPLE 1 herein, a plot of 'Sanitation Index' values over time. Reference lines for mean, performance target and upper confidence limit (UCL) are included to facilitate the application of principles of Statistical Process Control.

In the graph of FIG. 2, the Sanitation Index has been plotted over a period of 30 days. The plot also displays 'trend indicators' consistent with the basic principles of Statistical Process Control which allow meaningful preemptive and preventative decisions to be made regarding control of E. coli O157:H7. The trend indicators are:

Monthly mean—a measure of the central tendency of the Sanitation Index over time;

Upper Confidence Limit—calculated as 3-times the standard deviation of the Sanitation Index values composing the monthly mean, and represents a measure of the variability of the Sanitation Index, and a way to identify Sanitation Index values which require remediation action;

Performance Target—a value based on experience about what is possible from the theoretical optimum operation of intervention strategies and what is observed at facilities known to be run well; and Sequences of Sanitation Index values—Note the upward trend from Jan. 5, 2004 to Jan. 14, 2004. The trend is suggestive of the breakdown of a microbial intervention process and the subsequent "leakage" of index organisms through to the finished product. The problem was identified and fixed on Jan. 14, 2004. The Sanitation Index immediately reflected the change, as shown by the subsequent values from Jan. 15, 2004 onward.

EXAMPLE 2

Inventive Microbial Monitoring Methods were Applied to a High Volume Beef Production Facility to Provide for Process Control This EXAMPLE describes another exemplary application of particular aspects of the inventive microbial monitoring methods to the beef industry.

Rationale.

Qualitative pathogen testing, by its nature, typically results in strictly a positive or negative result. As describe above, in addition to the standard result of positive or negative for a give pathogen, multiplex PCR (and/or other assays) allows for determination of negative or positive results for index organisms (e.g., for related coliform bacteria, or associated conditions or attributes). PCR bands indicating the presence, for example, of shiga-like toxin production, or indicating the ability for an organism to attach and efface do not necessarily indicate a target profile (e.g., pathogenic profile; e.g., E. coli O157:H7); that is, frequently, these nonspecific bands are associated with other index organisms (e.g., coliform bacteria, or associated conditions or attributes) exhibiting these abilities. Only when these bands are associated with the E. coli O157 specific rfb PCR band, for example, does the test indicate a pathogenic profile. Quantifying a qualitative test may, for example, be accomplished by dividing the number of observed bands by the total number of possible bands, where the resulting number is referred to herein as an index value. The use of such indexing for process control (e.g., statistical process control), centers on a critical assumption; namely, that the presence of one or more index organisms (e.g., a more common coliform, or associated conditions or attributes) will serve as a predictive precursor to the appearance of a less common target microbe (e.g., pathogenic *E. coli* O157).

Data for this EXAMPLE was collected from a high volume beef production facility located in the Midwest United States. The distribution of band patterns was studied for 25,698 samples collected from the same beef production facility for a calendar year. The results of this study show that the most prevalent occurrence, 74.85 percent of the samples, was the detection of no multiplex PCR bands (19,236 of 25,698). When Multiplex PCR bands were detected, the most common result was the detection of the individual multiplex PCR bands. Significantly, no band combination, for example the "B" and "C" combination, was more prevalent than the individual bands making up the combination signal (TABLE 1). The detection of multiple multiplex PCR bands, therefore, is most often the result of multiple independent organisms generating multiple signals. The question of whether the bands of a pathogenic profile are mutually associated is determined through the 'conformation' process. A conformation indicating a common, pathogenic, source in this study occurred 50 times out of the 25,698 samples collected. Individual bands and the combination of individual bands, when quantitatively and temporally tracked as an index, act as a precursor (i.e., harbinger) to pathogenic production failure (the presence of more common coliform effectively act as a precursor to the appearance of the less common pathogenic *E. coli* O157).

Figure 3:
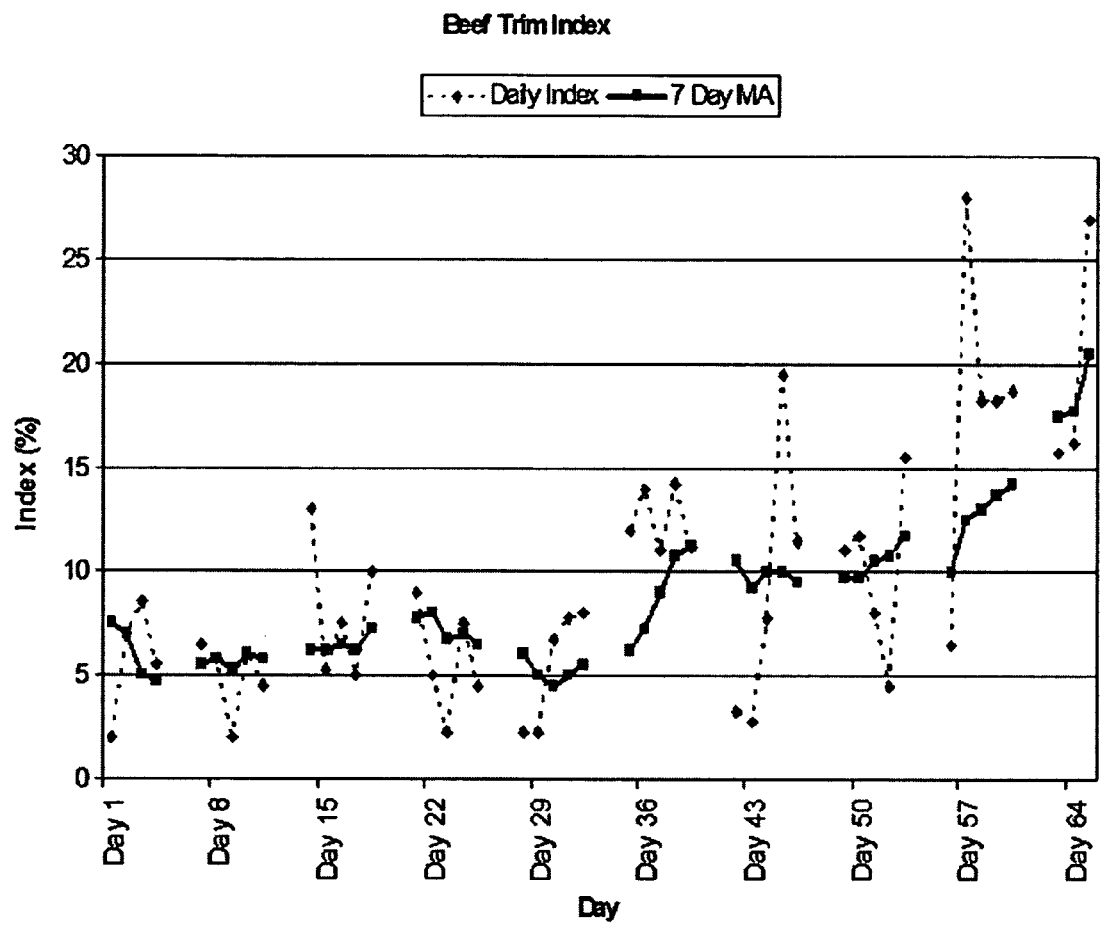
FIG. 3 shows, according to EXAMPLE 2 herein, a plot of the inventive index value over time (plotted daily and as 7 day moving average) as applied to harvested beef product (trim), showing multiple rapid increases in the trim index that can be used for process control.

FIG. 3 shows a plot of the index values over time, and depicts a plurality of rapid increases in the trim index. Through this period, nine (9) confirmed cases of pathogenic *E. coli* O157 were detected. According to aspects of the present invention, when the index is tracked by 'shift' (working shift), it provides key indications regarding the process and the type of failure that is occurring. Process failures can, for example, be classified as mechanical process failures or as employee process failures.

Figure 4:
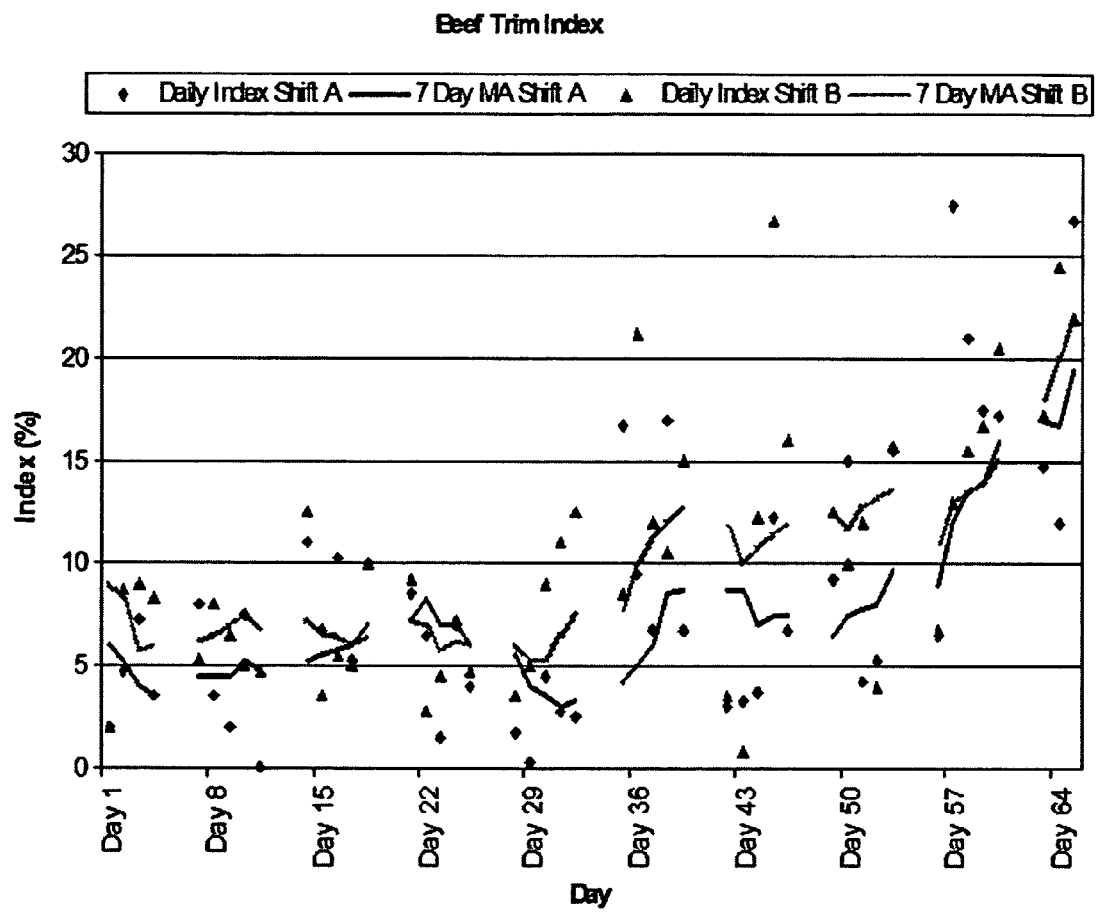
FIG. 4 shows, according to EXAMPLE 2 herein, and for the same data and period as in FIG. 3, the inventive index values (plotted as 7 day moving average.) sorted by 'shift' (A and B working shifts). The curves are indicative of mechanical process failure.

FIG. 4 shows the index separated by 'shift' for the same period as FIG. 3. The fact that the respective index for both shifts coordinately increased at the same tempo indicates a mechanical process failure; a failure that is consistent across both shifts. By contrast, an employee process failure, for example, would appear as a significant variance between the respective index values.

Figure 5:
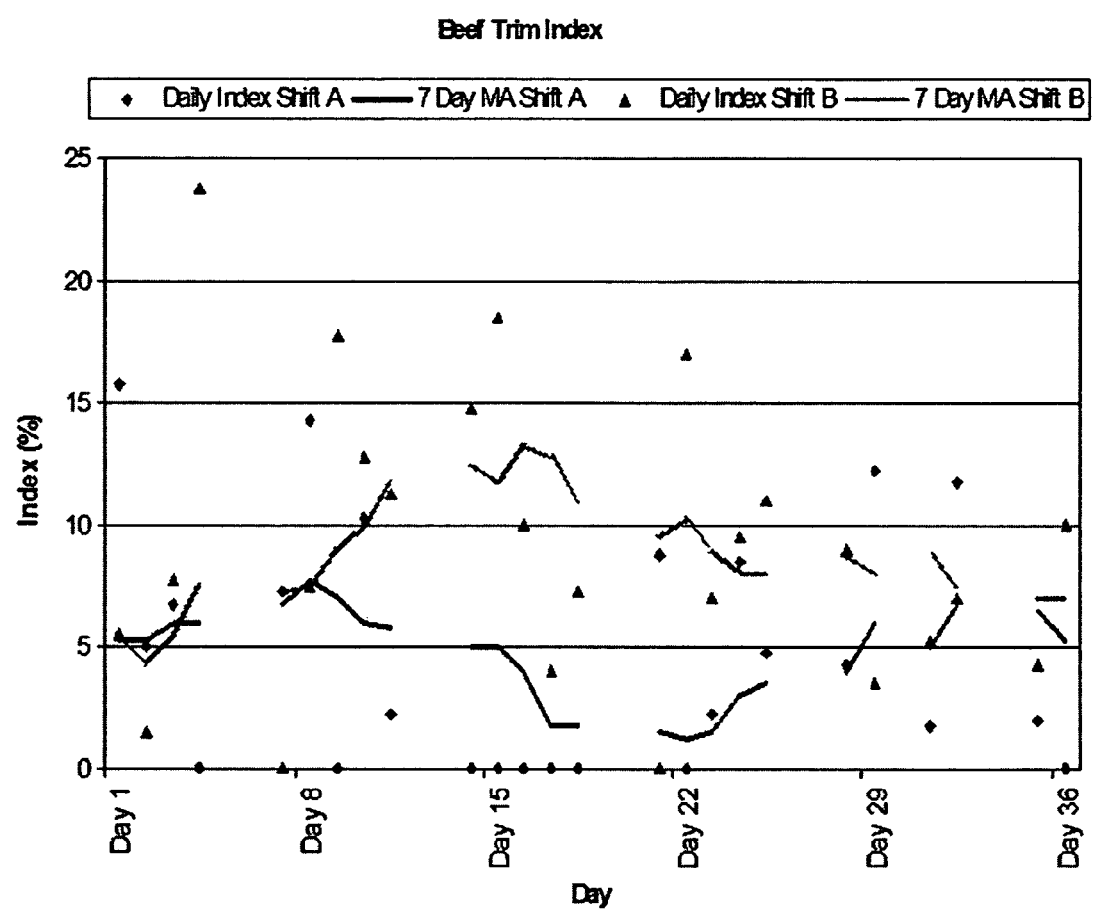
FIG. 5 shows, according to EXAMPLE 2 herein, and using the same data set as that used in FIGS. 3 and 4, that over approximately a month period of time the index values of one shift "A" significantly varied from those of the other "B." During this period, one confirmed case of pathogenic *E. coli* O157 was detected on the "A" shift.

FIG. 5 demonstrates that, over approximately a one month period of time, the index values of one shift "A" significantly varied from those of the other "B." During this period, one confirmed case of pathogenic *E. coli* O157 was detected. The product involved in this case was produced on "A" shift. Index values may also be established on carcasses tested for pathogenic *E. coli* O157. This is typically done immediately after the slaughter operation. Indexing at this point in the process provides another proactive opportunity to reduce pathogenic bacteria from the manufacturing process. "Dirty" carcasses proceeding into a fabrication process will result in "dirty" trim. The reverse is, however, not always the case. "Clean" carcasses entering into fabrication do not always result in "clean" trim, because multiple variables may introduce pathogenic *E. coli* after the point at which hot carcasses are tested. Therefore, no strict correlation exists between the carcass index and the fabrication trim index.

TABLE 1

Multiplex PCR Band Distribution

| Pattern | Pattern Incidence (%) | ASSAY (O157 antigen) | O157 (PCR A) | EAE (PCR B) | SHIGA 2 (PCR C) | SHIGA 1 (PCR D) | Number of Samples |
|---|---|---|---|---|---|---|---|
| 1 | 74.85% | — | — | — | — | — | 19236 |
| 2 | 22.90% | — | — | — | X | — | 1480 |
| 3 | 19.62% | — | — | X | — | — | 1268 |
| 4 | 8.45% | — | — | X | X | — | 546 |
| 5 | 8.19% | — | — | — | — | X | 529 |
| 6 | 7.35% | — | — | — | X | X | 475 |
| 7 | 6.92% | — | — | X | X | X | 447 |
| 8 | 6.48% | — | X | — | — | — | 419 |
| 9 | 4.09% | — | X | X | X | X | 264 |
| 10 | 2.80% | — | — | X | — | X | 181 |
| 11 | 2.41% | — | X | — | X | — | 156 |
| 12 | 2.04% | — | X | X | — | — | 132 |
| 13 | 1.55% | — | X | X | X | — | 100 |
| 14 | 1.49% | X | — | — | — | — | 96 |
| 15 | 1.42% | X | X | — | — | — | 92 |
| 16 | 1.35% | — | X | — | X | X | 87 |
| 17 | 0.76% | — | X | — | — | X | 49 |
| 18 | 0.43% | X | X | — | X | — | 28 |
| 19 | 0.31% | X | X | X | — | — | 20 |
| 20 | 0.31% | X | X | X | X | X | 20 |
| 21 | 0.23% | — | X | X | — | X | 15 |
| 22 | 0.20% | X | X | X | X | — | 13 |
| 23 | 0.17% | X | — | X | — | — | 11 |
| 24 | 0.12% | X | — | — | — | X | 8 |
| 25 | 0.11% | X | — | — | X | — | 7 |
| 26 | 0.08% | X | X | — | — | X | 5 |
| 27 | 0.06% | X | — | X | X | — | 4 |
| 28 | 0.06% | X | X | — | X | X | 4 |
| 29 | 0.05% | X | — | — | X | X | 3 |
| 30 | 0.03% | X | — | X | X | X | 2 |
| 31 | 0.02% | X | X | X | — | X | 1 |

EXAMPLE 3

Inventive Microbial Monitoring Methods were Applied to Identify Individual Combos as the Source of a Positive Test This EXAMPLE describes yet another exemplary application of particular aspects of the inventive microbial monitoring methods to the beef industry.

When assigning specific combos to a 'Lot' (combination of 'combos'; combination bin of trim samples—typically five combos/Lot), beef production facilities frequently mix and match combos (sample bins containing trim). Typically, these combos are produced from different production lines at different times. Where a respective trim sample (Lot sample) tests positive for a particular pathogen, it is, therefore, difficult to troubleshoot the production process to determine which combo of a Lot is contaminated. Aspects of the present invention (e.g., using multiplex testing) in conjunction with individual combo testing provide proactive methods affording reductions of pathogenic bacteria.

Samples.

The samples for this EXAMPLE were submitted by a large-scale beef operation located in the Midwest United States.

Methods.

Samples were collected by the production facility. Each sample consisted of a 375 gram sample. The 375 gram sample was evenly split between the combos making up the Lot. For example, a lot consisting of five combos was submitted to the lab as five bags each containing approximately 75 gram. Each of the individual bags was enriched separately and incubated for 8 hours. After incubation, a wet composite of the five individual bags was prepared. The composite sample was screened using Multiplex PCR technology. Suspect samples were further analyzed using immunomagnetic beads followed by additional analysis utilizing Multiplex PCR technology. The secondary analysis was performed on the composite sample as well as each of the individual sub samples.

Results.

This method has proven to be a beneficial means of proactively troubleshooting beef production facilities to reduce the presence of pathogenic bacteria. Samples confirmed as positive using this method are readily traced to individual combos. Using this information, production facilities can quickly identify common product types, production lines, or carcass lots used in the producing these specific combos.

Figure 6A:
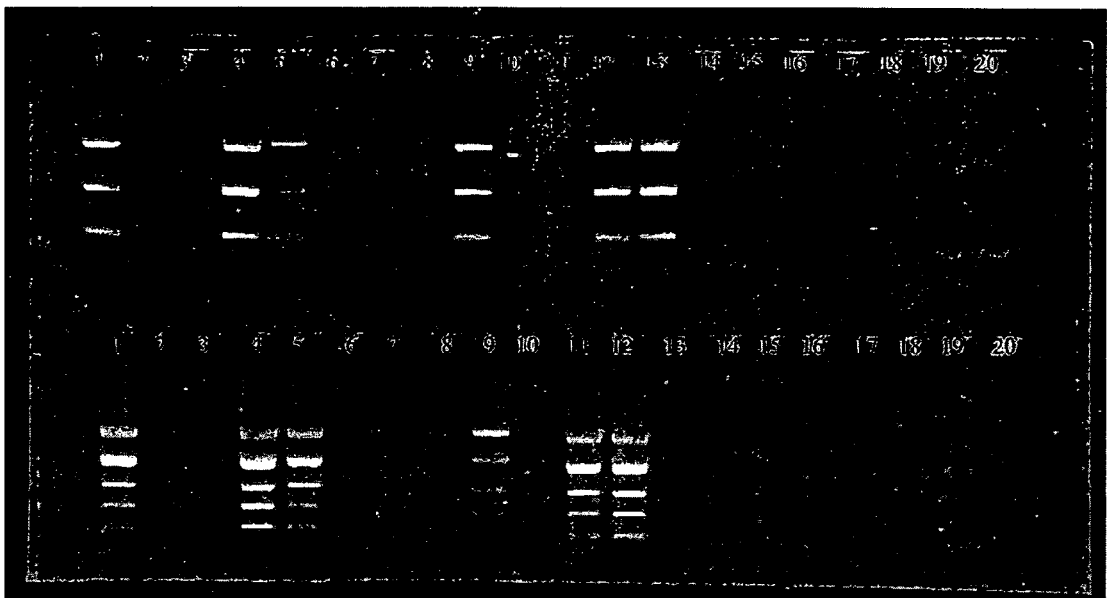
FIG. 6A (upper gel) shows a multiplex PCR analysis of samples from individual sub-lots ('combos'), showing that the individual sub lots that tested positive were comprised of 'chuck trim,' while the negative testing sub-lots consisted of various non-chuck trim products. The data enables the production facility to efficiently utilize resources in addressing only particular anatomicalcarcass areas, and those specific production lines associated with the production of that anatomical area (e.g., chuck trim).
Figure 6B:
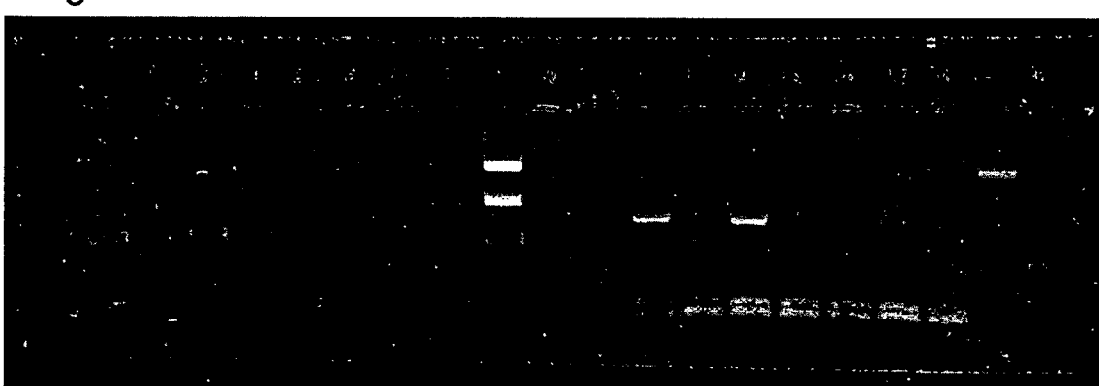
FIG. 6B (lower part) shows a negative multiplex PCR analysis in which a composite sample initially showed a suspect positive result, but yielded a negative confirmation. Though the test yielded a negative result, the individual sub-lot results revealed that sub lot B was the source of the suspect result. The data can be used in the same manner as a positive test result to identify which common product codes, production lines or lots of carcasses are carrying index organisms.

With reference to FIG. 6A (showing two rows of gel lanes), lane 1 in each row provides a confirmed positive composite sample for *E. coli* O157:H7. This particular composite analyzed consisted of five sub-samples (combo samples), referred to as sub samples A through E. Lanes 2 through 6 of each row represented these individual sub-samples. Sub-samples C and D were determined to be the source of the positive test, based on the analysis. Lane 12 of each row represents another composite sample that consisted of five sub-lots referred to as sub-samples A through E. Lanes 13 through 17 of each row represent these individual sub-samples. Sub-lot A was the source of the positive result, based on the analysis. The same analysis method can be used on samples that initially display as being suspect, and are subsequently shown to be negative. For example, in another exemplary analysis (FIG. 6B), a composite sample (lanes 1 and 12) was analyzed, consisting of five sub-lots (lanes 2 through 6, and 13 through 17). The image showed a negative conformation for *E. coli* O157:H7. However, it was determined that sub-lot B was the source of the suspect result. This information can be used in the same manner as a positive test result to proactively determine common product codes, production lines, or lots of carcasses used in producing this specific combo.

EXAMPLE 4

Inventive Multi-Target Microbial Monitoring (e.g., Using Multiplex PCR) Methods were used to Identify Potential Problems in Beef Production This EXAMPLE describes yet another exemplary application of particular aspects of the inventive microbial monitoring methods to the beef industry.

Rationale.

Troubleshooting of a beef production facility is greatly enhanced when an individual combo or combos are identified as the source of the positive test. According to aspects of the present invention, and using Multiplex PCR technology as the method for multi-target analysis, individual combos may be identified as the source of a positive test result, and such analyses may be conducted over time. Specific information obtained from this multi-targeted microbial monitoring method are then utilized to pinpoint production problems, and afford the opportunity for proactive efforts in reducing, for example, pathogenic bacteria from a production process.

Results.

Results where obtained from samples submitted by a large scale beef operation located in the Midwest United States.

Methods.

Samples were collected and processed as described in previous case study of EXAMPLE 3, outlining the identification of an individual combo or combos as the source of a positive test result. For each of the described samples, additional information was collected consisting of production time and product type, and this additional information was analyzed for commonalities that could logically direct the investigation.

Results.

As an example of the data collected, and with further reference to FIG. 6 (show two rows of lanes), lane 1 in each row shows a confirmed positive composite sample for *E. coli* O157:H7. This particular composite consisted of five sub-samples referred to as sub samples A through E. Lanes 2 through 6 of each row represent these individual sub-samples. As described above, sub-samples C and D were determined to be the source of the positive test. Lane 12 of each row represents another composite sample that consisted of five sub-lots referred to a sub-samples A through E. Lanes 13 through 17 of each row represent these individual sub-samples. As described above, sub-lot A was determined to be the source of the positive result.

Interpretation of Statistical Process Control (SPC) Charts Generated from "Sanitation Indices" Derived from Pathogen Profiles The following exemplary process control "Demonstrations" were enabled by the inventive methods in view of production time and product type analyzed for commonalities:

Demonstration 1.

Multi-targeted microbial Monitoring methods were used to show that decreasing "carcass sanitation index" was associated with a coordinate reduction of "trim sanitation index."

Figure 7:
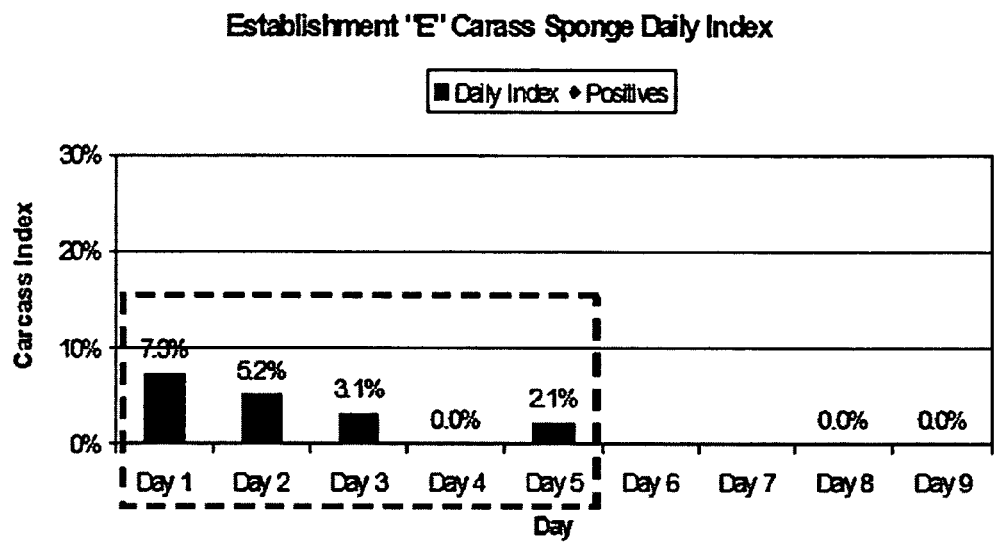
FIG. 7 shows, for establishment 'E,' a temporal plot of "Carcass Index" (i.e., "Carcass Sponge Daily Index") derived from sponge sampling of carcasses at various time points. Carcass Sponge Samples are collected from carcasses which are processed to produce beef trim products, and precede beef trim samples by approximately 24 hours.
Figure 8:
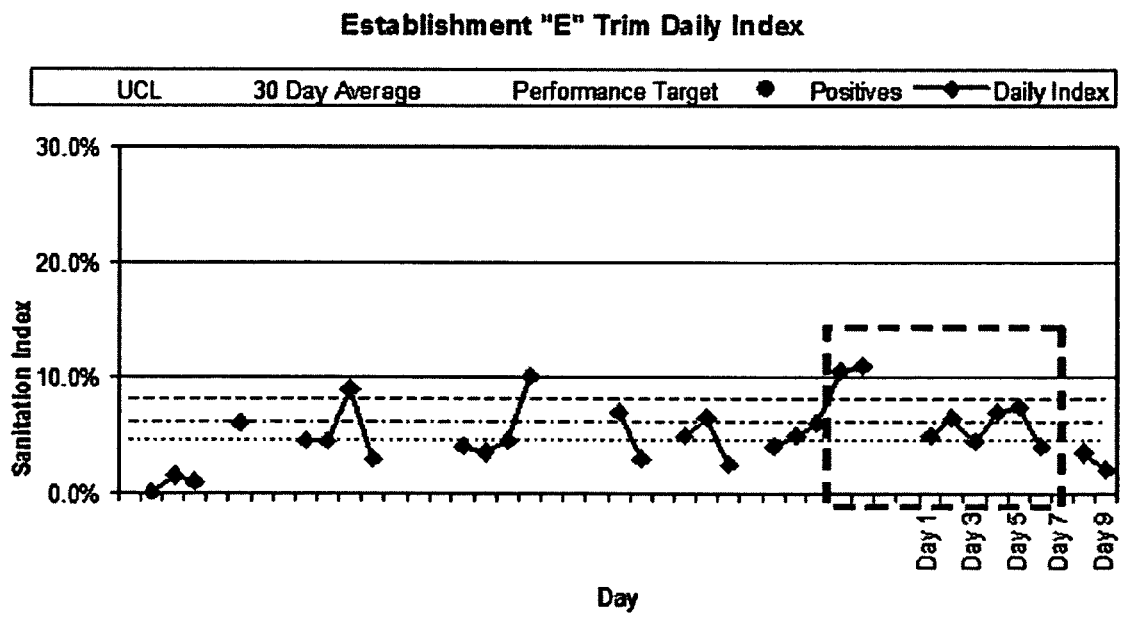
FIG. 8 shows a temporal plot of "Sanitation Index," as described herein, for the same establishment as in FIG. 7, and including a corresponding time period (highlighted by dashed boxes). The data shows that decreasing carcass sanitation index (FIG. 7) was correlated with a coordinate reduction of trim sanitation index (FIG. 8).

FIG. 7 shows, for establishment 'E,' a temporal plot of "Carcass Index" (i.e., "Carcass Sponge Daily Index") derived from sponge sampling of carcasses at various time points. For comparison, FIG. 8 shows a temporal plot of trim "Sanitation Index," as described herein above, for the same establishment, and corresponding temporal sampling ranges between the analyses of FIGS. 7 and 8 are highlighted by dashed boxes. The data shows that decreasing carcass sanitation index was associated with a coordinate reduction of trim sanitation index.

Demonstration 2.

Multi-targeted microbial Monitoring methods were used to show that high "carcass sanitation index" was a harbinger of increasing "trim sanitation index," as well as of the presence of *E. coli* O157:H7 in 'trim.'

Figure 9:
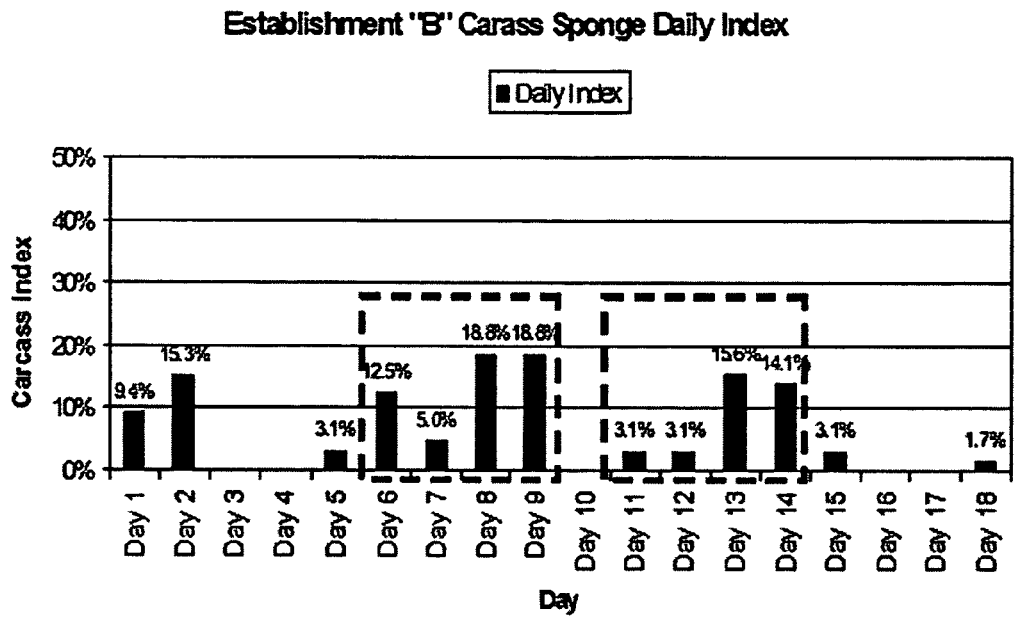
FIG. 9 shows, for establishment "B" a temporal plot of "Carcass Index" in which elevated values of the index are observed for two periods (highlighted by dashed boxes).
Figure 10:
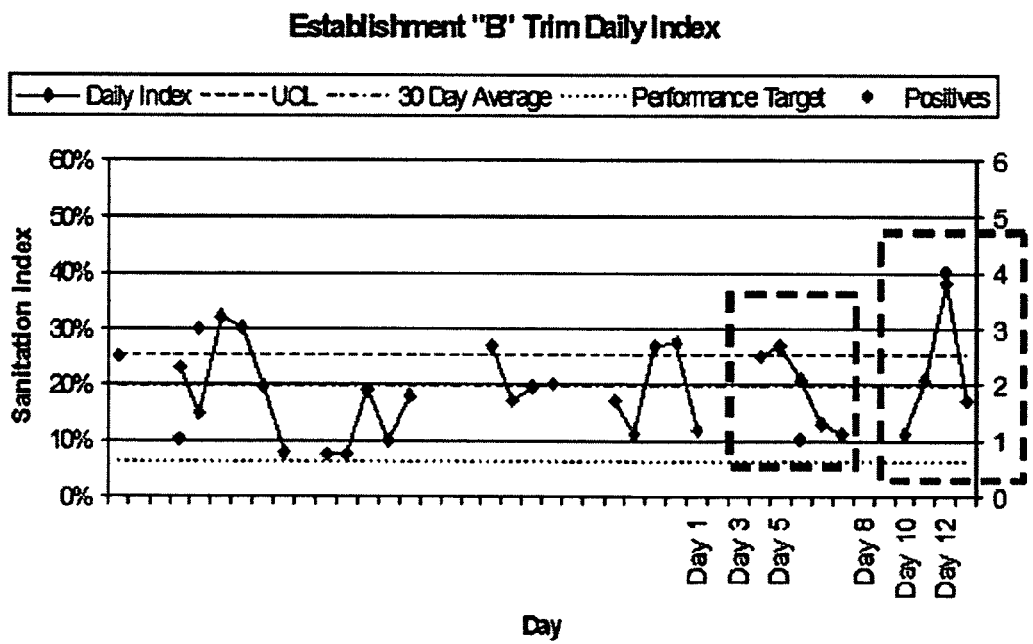
FIG. 10 shows a temporal plot of "Sanitation Index" and the presence of positive results (presumptive) for *E. coli* O157 for beef trim produced from the carcasses sampled in FIG. 9. The data shows that the increasing carcass sanitation index (FIG. 9) was correlated with a coordinate increase of trim sanitation index and the appearance of positive results (presumptive) for *E. coli* O157.

FIG. 9 shows, for establishment 'B,' a temporal plot of "Carcass Index" (i.e., "Carcass Sponge Daily Index") derived from sponge sampling of carcasses at various time points. For comparison, FIG. 10 shows a temporal plot of trim "Sanitation Index," as described herein above, for the same establishment, and corresponding temporal sampling ranges between the analyses of FIGS. 9 and 10 are highlighted by dashed boxes. The data shows that high "carcass sanitation index" was a harbinger of increasing "trim sanitation index," as well as of *E. coli* O157:H7 in 'trim' (one positive event is shown in each box of FIG. 10).

Demonstration 3.

Multi-targeted microbial Monitoring methods were used to show that high "carcass sanitation index" was a harbinger of increasing "trim sanitation index," as well as of the presence of *E. coli* O157:H7 in 'trim.'

Figure 11:
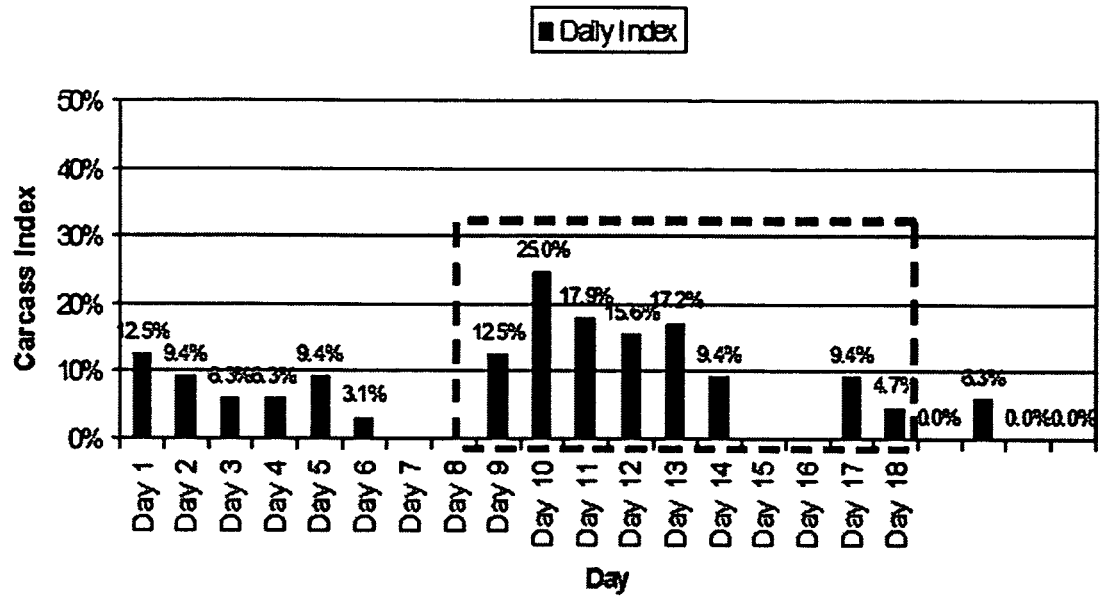
FIG. 11 shows for establishment "E" a temporal plot of "Carcass Index" in which elevated values of the index are observed for a period (highlighted by dashed box) similar to FIG. 9.
Figure 12:
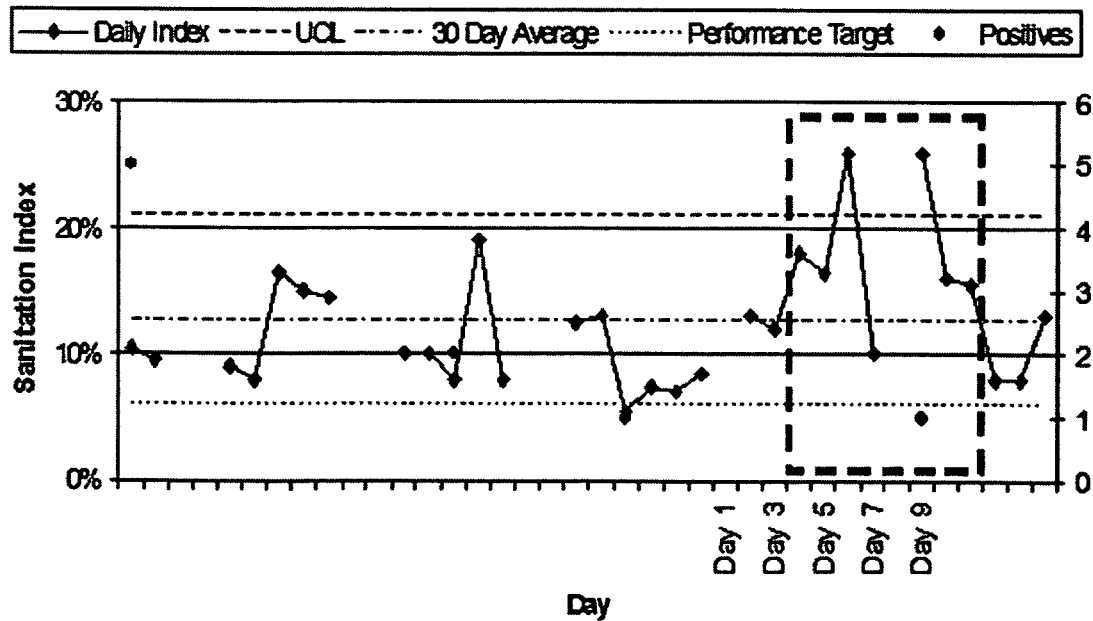
FIG. 12 shows that similar to FIG. 10 a temporal plot of "Sanitation Index" and the presence of positive results (presumptive) for *E. coli* O157 for beef trim produced from the carcasses sampled in FIG. 11 was correlated with a coordinate increase of trim sanitation index and the appearance of positive results (presumptive) for *E. coli* O157.

FIG. 11 shows, for establishment 'E,' a temporal plot of "Carcass Index" (i.e., "Carcass Sponge Daily Average Index") derived from sponge sampling of carcasses at various time points. For comparison, FIG. 12 shows a temporal plot of trim "Sanitation Index," as described herein above, for the same establishment, and corresponding temporal sampling ranges between the analyses of FIGS. 11 and 12 are highlighted by dashed boxes. The data shows that high "carcass sanitation index" was a harbinger of increasing "trim sanitation index," as well as of *E. coli* O157:H7) in 'trim' (one positive event is shown in the box of FIG. 12).

Demonstration 4.

Multi-targeted microbial Monitoring methods were used to show that high 'trim' "Sanitation Index" was a harbinger of the presence of *E. coli* O157:H7 in 'trim.'

Figure 13:
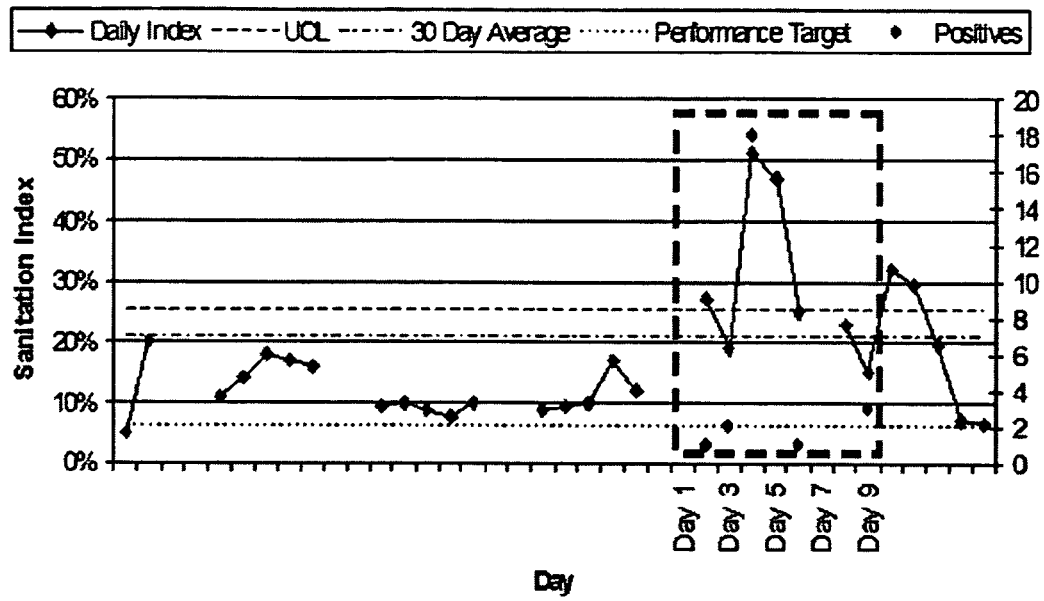
FIG. 13 shows a temporal plot of "Sanitation Index" and the presence of positive results (presumptive) for *E. coli* O157. The data show that increasing trim sanitation index was correlated with an increased incidence of positive results (presumptive) for *E. coli* O157.
Figure 14:
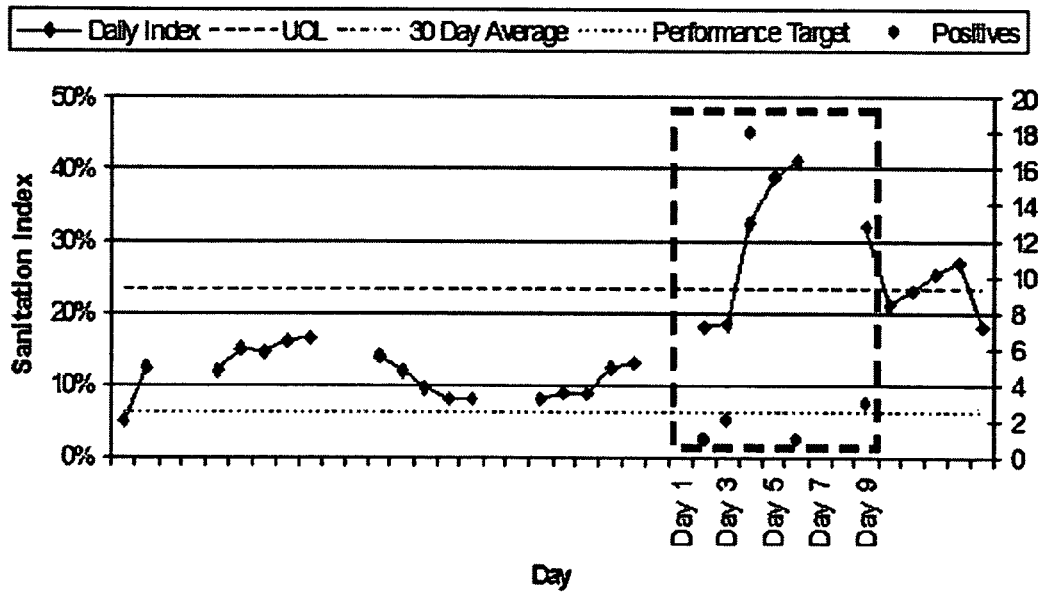
FIG. 14 shows the same data as in FIG. 13, except plotted as a 3 day moving average.

FIG. 13 shows, for establishment 'B,' a temporal plot of trim "Sanitation Index" (as defined herein) derived from trim sampling at various time points, and plotted as 'daily index' values For comparison, FIG. 14 shows a temporal plot of trim "Sanitation Index" for the same establishment, but plotted as '3-day moving average' (MA) values. Corresponding temporal sampling ranges between the analyses of FIGS. 13 and 14 are highlighted by dashed boxes. The data shows that high 'trim' "Sanitation Index" was a harbinger of the presence of *E. coli* O157:H7 in 'trim' (five positive events are shown in the box of FIG. 14).

Demonstration 5.

Multi-targeted microbial Monitoring methods were used to show that continuous high 'trim' "Sanitation Index" correlated with continuous presumptive *Salmonella* in 'trim.'

Figure 15:
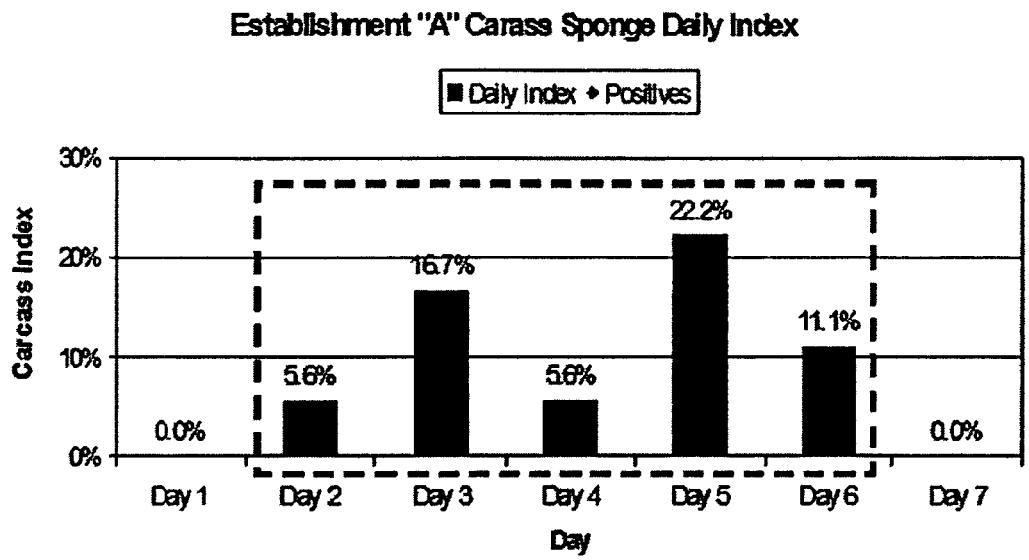
FIG. 15 shows a temporal plot of "Carcass Index" for establishment "A" in which elevated values of the index are observed for a period (highlighted by dashed box). In this case the carcass index was constructed from a 7 factor system in which 2 *Salmonella* specific markers were added to the 5 *E. coli* markers.
Figure 16:
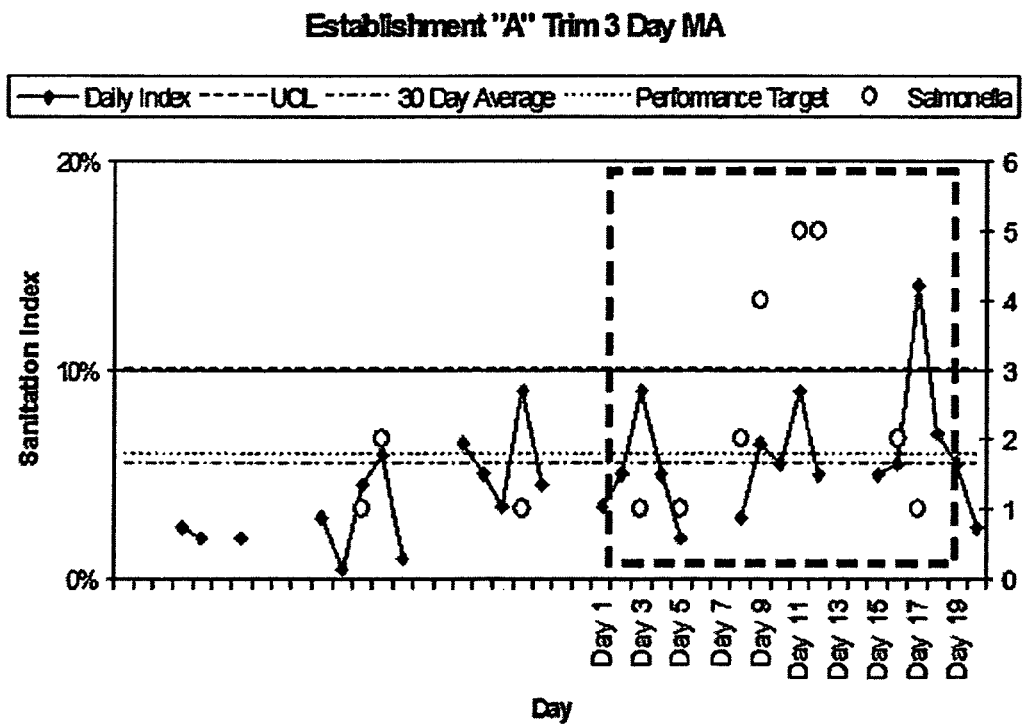
FIG. 16 shows a temporal plot of "Sanitation Index" and the presence of positive results (presumptive) for *Salmonella* for beef trim produced from the carcasses sampled in FIG. 15. The data shows that the increasing carcass sanitation index (FIG. 15) was correlated with a coordinate increase of trim sanitation index and the appearance of positive results (presumptive) for *Salmonella*.

FIG. 15 shows, for establishment 'A,' a temporal plot of "Carcass Index" (i.e., "Carcass Sponge Daily Average Index") derived from sponge sampling of carcasses at various time points, and plotted as 'daily index' values For comparison, FIG. 16 shows a temporal plot of trim "Sanitation Index" for the same establishment. Corresponding temporal sampling ranges between the analyses of FIGS. 15 and 16 are highlighted by dashed boxes. The data shows that continuous high 'trim' "Sanitation Index" correlated with continuous presumptive *Salmonella* in 'trim.'

Demonstration 6.

Multi-targeted microbial Monitoring methods were used to show that increasing "carcass sanitation index" was a harbinger of increasing "trim sanitation index," as well as of the presumptive presence of *E. coli* O157:H7 in 'trim,' and further show that corrective actions could be taken in the plant to consequently reduce both carcass and trim indices.

Figure 17:
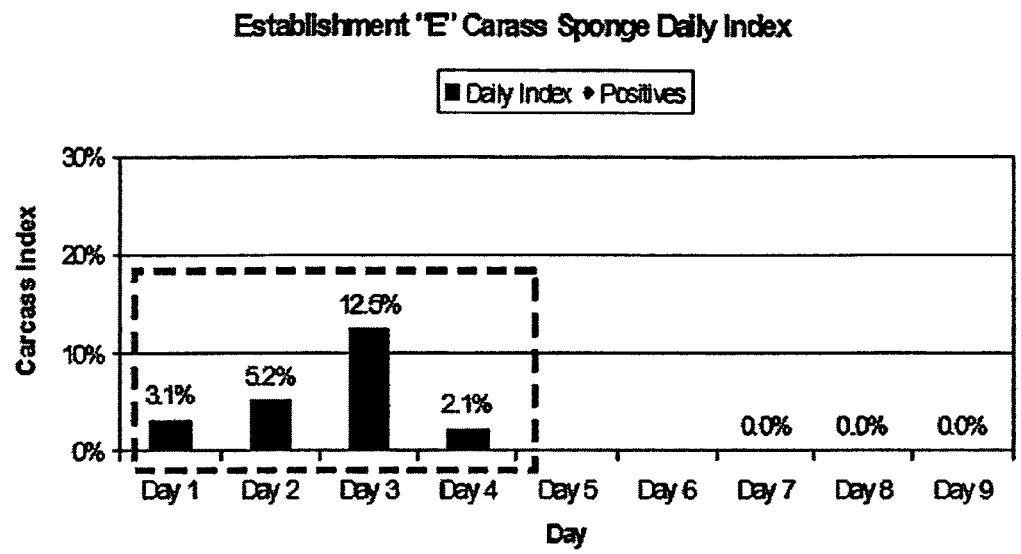
FIG. 17 shows a temporal plot of carcass sanitation index, showing a period of time where the index was elevated (highlighted by the dashed box). After corrective actions were taken by the plant, subsequent values of the carcass sanitation index are lowered.
Figure 18:
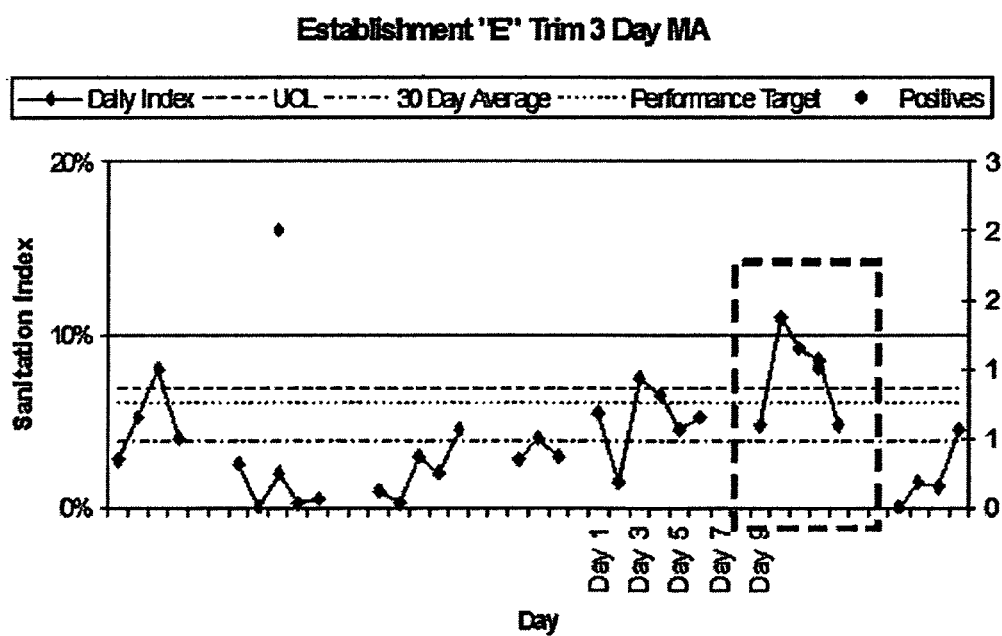
FIG. 18 shows a temporal plot of the sanitation index for beef trim produced from the carcasses sampled in FIG. 17. The data show increased values in the index followed by a decline which were correlated with the carcass sanitation index in FIG. 17.

FIG. 17 shows, for establishment 'E,' a temporal plot of "Carcass Index" (i.e., "Carcass Sponge Daily Average Index") derived from sponge sampling of carcasses at various time points, and plotted as 'daily index' values For comparison, FIG. 18 shows a temporal plot of trim "Sanitation Index" for the same establishment. Corresponding temporal sampling ranges between the analyses of FIGS. 17 and 18 are highlighted by dashed boxes. The data shows that increasing "carcass sanitation index" was a harbinger of increasing "trim sanitation index," as well as of the presumptive presence of *E. coli* O157:H7 in 'trim,' and further show that corrective actions could be taken in the plant to consequently reduce both carcass and trim indices.

Summary of the Above Examples and Demonstrations

Aspects of the present invention solve a long-standing problem in the art; namely, the inability to apply the results of prior art microbial detection/monitoring methods for purposes of process or system control (e.g. statistical process control; SPC).

Prior Art Microbial Detection/Monitoring Methods are Deficient.

As stated herein above, prior art methods for microbial detecting and monitoring are divided into two broad groups: (i) direct specific detection of the target microbe by determining a presence or absence status for a presumably 'target microbe-specific' marker or characteristic; and (ii) indirect detection, based on determining a presence or absence status for a presumably 'indicator microbe-specific' marker, which if present is deemed to be indicative of the presence of the target microbe. As further discussed herein, these two approaches have two fundamental problems by virtue of being premised on isolated presence/absence tests that yield only an isolated presence/absence signal. First, because of Type 1 and 2 errors, a single test cannot always be regarded as a definitive measure of whether the microbial behavior is present or absent. Second, prior art detection schemes are not effectively applicable to statistical process control (SPC), because for the majority of samples tested by such prior art presence/absence detection schemes, the particular 'target' or 'indicator' microbes are either not present, or are present at undetectable levels, giving rise to numerous isolated negative values that cannot be effectively used in SPC to provide early warning of process failure, exposure and risk assessment, and to facilitate risk based decision making.

Solution to Prior Art Deficiency Provided by Aspects of the Present Invention.

As described and disclosed herein, aspects of the present invention derive, relative to prior art methods, additional information from microbial marker test results for samples which have tested negative for the presence of a target microbe, or microbe-associated property of attribute (e.g., pathogens, such as *E. coli* O157:H7, etc.). Partially-positive results (i.e., negative results for a particular target microbe or associated condition or attribute, which are nonetheless positive for a subset of markers) are indicative of the presence of index organisms (or index organism-associated conditions or attributes) that are genetically distinct, but which nonetheless share genetic, metabolic, behavioral, etc., characteristics with a given target microbe (e.g., *E. coli* O157:H7). By preparing an index value (e.g., "Sanitation Index value") based on the partially-positive results, and temporally tracking the Sanitation Index values, trends are identified, thus affording application of the principles of Statistical Process Control to direct meaningful preemptive, preventative and remedial action to control a given microbial process or system.

Therefore, the presently disclosed extended analysis of information derived from the inventive microbial sampling and monitoring methods overcomes substantial limitations in the prior art. The inventive methods are pro-active, utilizing index organisms whose presence is a harbinger of (indicates the probability of), for example, appearance of a target microbe in a process or system (e.g., a harbinger of 'leakage' of *E. coli* O157:H7 into a beef fabrication facility). By providing an early indicator, preemptive and preventative actions can be taken to maintain or control the process or system, before imbalance occurs (e.g., before products become contaminated. The inventive microbial monitoring methods provide viable economic solutions and alternatives, whereby a range of controls, remedial actions, etc., may be applied when trends, not previously observable using prior art methods, are observed in the inventive microbial monitoring indices (e.g., changes in the "Sanitation Index"). Such process control has substantial utility, because the range of applicable controls, remedial actions, etc., are far less expensive than loss of process/system time, and concomitant destruction of product.

Significantly, the inventive microbial monitoring methods will finally enable the type of meaningful, preventative monitoring of process and systems that federal agencies are seeking (e.g., USDA). For example, while the USDA Food Safety and Inspection Service has encouraged the use of 'count' data in this manner, most *E. coli* count data points fall below the limit of detection in clean/semi-clean environments. Moreover, such counts lack the fundamental predictive advantage of monitoring for shared index markers that the present invention affords and exploits. Thus, it is evident that SPC cannot be effectively applied using, for example 'count' data, and particularly when the majority of the data points do not allow identification of meaningful (relevant) trends. Therefore, the present invention not only solves a long-standing problem in the art, and is not only economically highly beneficial, but also, for the first time, allows for meaningful regulatory oversight and control, and is profoundly in the broader public interest in view of the health benefits associated with properly managed processes and systems (e.g., abattoirs), and human lives likely to be saved by the present inventive methods.

Broad Applications

As stated above, the present inventive microbial monitoring methods have broad application. Particular embodiments provide methods for pathogen and organism profiling, and generating SPC charts for use in any industrial setting or process, or in any system that requires microbiological control of production, or microbial balance. Such applicable processes and systems include, but are not limited to: food production; manufacturing; processing; storage; transportation and distribution; with respect to microbial pathogens—process sanitation, environmental contaminants, and spoilage organisms; with respect to fermentation processes—determining purity of the seed stock and fermentation contaminants; aseptic processing (e.g., food and pharmaceutical; with respect to sterility and environmental control); water treatment (e.g., with respect to microbiological quality of the raw and treated water, and control of the organisms throughout the distribution system); wastewater treatment (e.g., with respect to microbiological quality of the treated wastewater and bio-solids, control of the treatment process, control of the aerobic and anaerobic digesters, and assessment of the impact of the discharged wastewater and application of bio-solids on the receiving environments); control of microbial contaminants and assessment of their impact in the indoor environment and indoor air quality assessment studies; environmental microbiology (e.g., with respect to monitoring the microbiological quality of shellfish, shellfish beds and cultured aquatic organisms, assessing the microbiological quality of recreational waters and swimming beaches, assessing the microbiological quality of bodies of water, conducting impact assessment of point and non-point-sources); feed microbiology (e.g., in determining the microbiological quality and safety of the feed); soil microbiology (e.g., in assessing the overall microbiology and population structure of soil organisms, in assessing target organisms that can indicate environmental contamination or organic and inorganic reservoirs (e.g., oil fields)).

Application of the inventive microbial monitoring assays encompasses a broad array of microbes and organisms including, but not limited to: pathogenic bacterial, viral, parasitic and fungal organisms (see, e.g., TABLE 2 below); spoilage microbes and organisms including, but not limited to those implicated in spoilage and/or fermentation of meat, eggs, seafood, milk, vegetables, fruits, beer, etc. (see, e.g., TABLE 3 below); 'beneficial organisms' including, but not limited to those implicated in dairy (fermentation) brewing (fermentation), meat (fermentation), bacteriocin production, probiotics, antibiotics, etc. (see, e.g., TABLE 4 below); microbial contaminants including, but not limited to bacterial, viral, fugal, etc. contaminants (see, e.g., TABLE 5 below); indicator organisms, including but not limited to food-born, airborne, waterborne, etc. (see, e.g., TABLE 6 below); and bioremediation organisms, including but not limited to those shown in TABLE 7 below.

TABLE 2

Examples of Pathogenic Organisms

|  | Foodborne | Airborne | Waterborne |
|---|---|---|---|
| Bacterial | *Bacillus cereus* | *Bacillus anthracis* | *Vibreo cholerae* |
|  | *Escherichia coli* O157:H7 | *Mycobacterium tuberculosis* | *Salmonella* spp. |
|  | *Listeria monocytogenes* |  |  |
| Viral | Norwalk-like viruses | Influenza | Norwalk-like viruses |
|  | Hepatitis A | SARS | Hepatitis A virus |

TABLE 2-continued

Examples of Pathogenic Organisms

|  | Foodborne | Airborne | Waterborne |
|---|---|---|---|
| Parasitic | Cryptosporidium parvum<br>Cyclospora cayetanensis<br>Giardia lamblia | Cysticercosis spp.<br>Cryptosporidium spp. | Cryptosporidium parvum<br>Giardia lamblia |
| Fungal | Aspergillus flavus<br>Aspergillus parasiticus | Aspergillosis<br>Cryptococcosis spp. | Aspergillus spp.<br>Candida albicans |

TABLE 3

Examples of Common Spoilage Organisms

| Food Product | Spoilage Organism(s) |
|---|---|
| Meat | Brochothrix thermosphacta |
|  | Enterobacteriaceae |
|  | Lactobacillus sake |
| Eggs | Pseudomonas spp. |
|  | Proteus vulgaris |
|  | P. intermedium spp. |
|  | Serratia spp. |
| Seafood | Leuconostoc gelidum |
|  | Leuconostoc gasicomitatum |
| Milk | Pseudomonas fluorescens |
|  | Pseudomonas fragi |
| Vegetables | Sclerotinia sclerotiorum |
|  | Fusarium spp |
|  | Colletotrichum lindemuthianum |
| Fruits | Colletotrichum musae |
|  | Plasmapara viticole |
|  | Certocystis paradoxa |
| Beer (Fermentation) | Lactobacillus brevis |
|  | Lactobacillus casey |
|  | Lactobacillus paracasei ssp. paracasei |
|  | Saccharomyces cerevisiae var. diastaticus |

TABLE 4

Examples of Beneficial Organisms

| Process | Organism(s) |
|---|---|
| Dairy (Fermentation) | Lactococcus lactis |
|  | Steptococcus thermophilus |
|  | Lactobacillus delbruekii |
|  | Streptococcus thermophilus |
| Brewery (Fermentation) | Saccharomyces cerevisceae |
|  | Saccharomyces carlsbergensis |
|  | Saccharomyces uvarum |
|  | Pediococcus spp. |
| Meat (Fermentation) | Lactobacillus hordniae |
|  | Lactobacillus xylosus |
|  | Lactobacillus fermentum, |
| Bacteriocin Production | Pediococcus spp. |
|  | Leuconostoc mesenteroides subsp. Meseteroides |
| Probiotics | Lactobacillus acidophilus |
| Antibiotics | Penicillium chrysogenum |
|  | Cephalosporium acremonium |
|  | Penicillium griseofulvum |
|  | Bacillus subtilis |
|  | Bacillus polymyxa |

TABLE 5

Example of Contaminants

|  |  | Food | Water | Air |
|---|---|---|---|---|
| Bacteria | | Acetobacter spp. | Coliform | Mycobacterium tuberculosis |
|  | | Acetomonas spp. | E. coli O157:H7 | M. bovis |
|  | | | Vibrio cholerae | M. avium |
|  | | | Salmonella typhi | |
|  | | | Shigella spp. | |
|  | | | Campylobacter jejuni | |
|  | | | Escherichia coli | |
|  | | | Legionella pneumophila | |
| Virus | | Flavivirus | Hepatitis A | Respiratory syncytial virus |
| Fungal | | Mucor spp. | | Aspergillus flavus |
|  | | Penicillium spp. | | Fusarium spp. |
|  | | Geotrichum spp. | | Cephalosporium spp. |
|  | | Cladosporium spp. | | Stachybotrys spp. |
|  | | Rhizopus spp. | | |
|  | | | | Trichoderma spp. |
|  | | Anisakis simplex | Giardia lamblia | |
|  | | | Cryptosporidium parvum | Penicillium spp. |
|  | | | Entamoeba histolytica | Stachybotrys chartarum |
|  | | | | Aspergillus fumigatus |

TABLE 6

Examples of Indicator Organisms

| Food | Water | Air |
|---|---|---|
| E. coli | E. coli | Aspergilus wentii |
| Pseudomonas putrefaciens | Citrobacter spp. | Rhizopus stolonifer |
| Zygosaccharomyces bailii | Enterobacter spp. | |
|  | Klebsiella spp. | |
|  | Streptococcus faecalis | |
|  | Bifidobacterium adolescentis | |
|  | F-specific RNA coliphages | |

TABLE 7

Examples of Bioremediation Organisms

| |
|---|
| Acinetobacter calcoaceticus |
| Agaricus bisporus |
| Klebsiella aerogenes |
| Leucothrix mucor |
| Lentinus odoides |
| Moraxelha osloensis |
| Phanerochaete chrysosporium |
| Pseudomonas acidovorans |
| Sphaerotilus natans |

Bioremediation

Hazardous waste sites often contain complex mixtures of pollutants which include a wide variety of organic contaminants. Microbial bioremediation of organic pollutants is a promising method of environmental cleanup. However, the classes of organic contaminants present can vary widely (comprising, for example, aliphatic hydrocarbons, aromatic hydrocarbons, and chlorinated hydrocarbons. In some cases specific contaminants such as polychlorinated biphenyls are of interest.). It is also a fact that the conditions present during bioremediation are not well characterized, both in terms of ability to sustain microbial growth and in terms of characterizing the microflora present.

According to additional aspects of the present invention, it is therefore desirable to prepare and monitor 'microbial performance index' (e.g., bioremediation performance index), based on the presence or absence of specific microbial markers (e.g., genetic markers, antigenic markers, metabolic markers, microbial behavioral characteristics, etc., and combinations thereof). Such a performance index can be prepared by an appropriate combination (as described and disclosed herein) of the +/− (presence/absence) signals of the microbial markers. Additionally, as in other applications of the inventive methods described herein, the indices (e.g., Sanitation Index, or Microbial performance index) may be modified by weighting the positive (or negative) scores of different factors to reflect input of environmental assessment data (e.g., indicating the preponderance of particular chemical contaminants, conditions, etc., which are present).

Representative, exemplary microbial markers for obtaining microbial/bioremediative performance index data include, but are not limited to:

aromatic oxygenase genes (of pollutant bio-degrading microorganisms; e.g. phenol monooxygenase, identified by PCR methods for example) (see, e.g., Baldwin et al., Detection and Enumeration of Aromatic Oxygenase Genes by Multiplex and Real-Time PCR, *Appl. Environ. Microbiol* 69(6): 3350-3358, 2003);

metabolic intermediates in the degradation of various aromatic contaminants (e.g., Catechol 2,3-Dioxygenase; using, e.g., PCR-based methods for monitoring bioremediation) (see, e.g., Mesarch et al., Development of Catechol 2,3-Dioxygenase-Specific Primers for Monitoring Bioremediation by Competitive Quantitative PCR, *Appl. Environ. Microbiol*. 66(2): 678-683, 2000);

16S markers (e.g., for *dehalococcoides* group, which is capable of degrading chlorinated hydrocarbons in bioremediation sites) (see, e.g., Hendrickson et al., Molecular Analysis of Dehalococcoides 16S Ribosomal DNA from Chloroethene-Contaminated Sites throughout North America and Europe, *Appl. Environ. Microbiol*. 68(2): 485-495, 2002);

markers for methanotrophs (e.g., markers for the pmoA gene, which encodes the PmoA subunit methane monooxygenase (pMMO)) (see, e.g., Hors et al., Detection of Methanotroph Diversity on Roots of Submerged Rice Plants by Molecular Retrieval of pmoA, mmoX, mxaF, and 16S rRNA and Ribosomal DNA, Including pmoA-Based Terminal Restriction Fragment Length Polymorphism Profiling, *Appl. Environ. Microbiol*. 67(9): 4177-4185, 2001);

markers for detection of detect *Rhodocyclus*-like beta-*Proteobacteria* (e.g., for detecting the ability to express enhanced biological phosphorous removal, e.g., using small subunit rRNA genes (ppk genes), fluorescent in situ hybridization (FISH), and dot blot analysis) (see, e.g., McMahon et al., Polyphosphate Kinase from Activated Sludge Performing Enhanced Biological Phosphorus Removal, *Appl. Environ. Microbiol*. 68(10): 4971-4978, 2002);

markers for detection of thiocyanate-degrading bacteria (e.g., thiocyanate hydrolase gene markers, detected, for example using fluorescent immunostaining technique with thiocyanate hydrolase-specific antibodies) (see, e.g., Yamasaki et al., Genetic and Immunochemical Characterization of Thiocyanate-Degrading Bacteria in Lake Water, *Appl. Environ. Microbiol*. 68(2): 942-946, 2002).

Spoilage Organisms

Beer Spoilage.

Identification of brewery isolates has traditionally been accomplished biochemically by determining the assimilation and fermentation patterns of a number of carbohydrates and nitrogen sources.[1] Biochemical identification is, however, not accurate in determining genotypic differences in beer spoilage microorganisms. For example, in breweries, *Lactobacillus brevis* is known as a representative beer-spoilage microorganism, but not all stains are harmful.[2] For quality control in a brewery, it would be beneficial to develop the means for accurate identification of beer-spoilage microorganisms and estimation of their beer spoilage ability.[2]

There is a need to develop a "Spoilage Index" for assessing the possibility of beer spoilage. Such an index would be proportional to the presence or absence of specific virulence factors associated with the microorganisms of concern. This would be more effective than attempting to detect the organisms directly, since in many cases the organisms are strains or species which are members of larger microorganism families. Below is a list of specific genetic targets, useful to identify possible beer-spoilage microorganisms from non-harmful strains:

Open reading frames 5 (ORF5) were found to be useful for differentiating beer-spoilage ability of *Lactobacillus paracollinoides*.[3] ORF were detected in the 12 beer-spoilage strains of *L. paracollinoides*, and not in the two nonspoilage variants;

*Lactobacillus* spp. LA2 (DSM15502) and related strains (LA2 group) possess strong beer-spoilage ability. The 16S rDNA sequence of LA2 strain is virtually indistinguishable from that of *L. collinoides*, generally considered to be nonbeer-spoilage bacteria. The 16-23S rDNA intergenic spacer (ITS) regions of *Lactobacillus* spp. LA2 and *L. collinoides* JCM1123T have been sequenced to identify a genetic marker to distinguish between the two groups. Sequence comparison analysis between *Lactobacillus* spp. LA2 and *L. collinoides* JCM1123T revealed that the two contiguously located nucleotides are absent in both ITS regions of *Lactobacillus* spp. LA2.[4]

The presence or absence of ORF5 homologues in *Lactobacillus brevis* was found to be highly correlated with the beer-spoilage ability of *L. brevis* strains, indicating this ORF is potentially a useful genetic marker capable of differentiating beer-spoilage strains among *L. brevis*.[5]

[1] Riboprinting and 16S rRNA Gene. Barney M, Volgyi A, Navarro A, Ryder D. *Appl Environ Microbiol*. 2001. 67 (2), 553-560.

[2] Classification and Identification of Strains of *Lactobacillus brevis* Based on Electrophoretic Characterization of D-lactate dehydrogenase: Relationship Between D-lactate dehydrogenase and Beer-Spoilage Ability. Takahashi, T., Nakakita, Y., Sugiyama, H., Shigyo, T., Shinotsuka, K. *Journal of Bioscience and Bioengineering*. 1999. 88 (5), 500-506.

[3]Genetic Marker for Differentiating Beer Spoilage Ability of *Lactobacillus paracollinoides* Strains Suzuki, K., Ozaki, K. & Yamashita, H. *Journal of Applied Microbiology.* 2004 97 (4), 712-718.

[4]Genetic characterization and Specific Detection of Beer-Spoilage *Lactobacillus* sp. LA2 and Related Strains. Suzuki, K., Koyanagi, M. & Yamashita, H. *Journal of Applied Microbiology.* 2004 96 (4), 677-683.

[5]Genetic Characterization of Non Spoilage Variant Isolated from Beer-Spoilage *Lactobacillus brevis* ABBC45[C].Suzuki, K., Koyanagi, M. & Yamashita, H. *Journal of Applied Microbiology.* 2004 96 (5), 946-953.

Water Organisms:

Wastewater. Wastewater contains many nutrients and is drawn from many different sources. For this reason, wastewater frequently harbors very high levels of microorganisms. Though many of these microorganisms are benign, or even beneficial for the degradation and stabilization of organic matter, others may be pathogenic or potentially pathogenic. A "pathogenic organism" is defined as one causing or capable of causing disease. Waterborne and water-related diseases caused by pathogenic microbes are among the most serious threats to public health today.

In order to effectively understand, assess, and control the potential environmental and human health threats of waterborne pathogens posed due to changing patterns of water use, increasing water pollution, aging wastewater treatment systems, and an inadequate knowledge of the sources and occurrence, there is a distinct need for surveillance of epidemiological factors associated with infectious disease outbreaks. The identification and control of threats posed by waterborne pathogens requires effective pathogen monitoring procedures.

Tests which lack specificity (such as coliforms, fecal coliforms or total plate counts) may not be an accurate indicator of potential pathogenicity. Furthermore, in some cases, the same strain or species may non-pathogenic under some conditions, but may express its pathogenicity in response to environmental stimuli. Thus, there is a need to develop a "Virulence Factor Activity Index" for assessing wastewater quality. Such an index would be proportional to the presence or absence of specific virulence factors associated with pathogens of concern. This would be more effective than attempting to detect the pathogens directly, since in many cases the pathogens are strains or species within members of larger non-pathogenic microorganism families.

The application of such an index will be advantageous from the following standpoints:

Water management programs may take a preventative approach to pathogen pollution and increase source water protection;

Identification of "hot spot" areas that require targeted monitoring and intervention;

Increase understanding of the ecology of pathogens in aquatic ecosystems; increase understanding of the environmental risk factors for predicting disease outbreaks; and, evaluate current emergency response capacity for pathogens.

A list of the most common waterborne pathogens is provided in Table 8, below. These pathogens have many characteristics in common such as their ability to spread by the fecal-oral route with water as the intermediate medium, and their inability reproduce outside of a host. Selected members of the group may have other traits in common. For example, chlorination is an effective intervention for the bacterial and viral pathogens.

TABLE 8

Waterborne Fecal-Oral Route Pathogens

| Type | Illness | Detection Issues | Molecular Targets |
|---|---|---|---|
| Bacteria | | | |
| *Salmonella* spp. *S. Typhimurium* | Salmonellosis Typhoid fever | Genus *Salmonella* consists of two species, *bongori* and *enterica*. Enterica consists of six subspecies. Only one, subspecies *enterica* is associated with disease, and even then mostly the serovar *Typhimurium*. | IS200-PCR - amplification of a short insertion sequence of about 708 bp specific to *Salmonella enterica* subsp. *enterica* serotype *Typhimurium*.[1] Differential patterns of acquired virulence genes distinguish *Salmonella* strains.[2] Use of microarrays to distinguish between strains of serovars.[3] Molecular basis for interaction of *salmonella* with intestinal mucosa, review article.[4] |
| *Shigella* | Shigellosis | | Numerous chromosomal and plasmid genes associated with virulence, review article. Partial list: aerobactin (iucABCCD and iutA), shiga toxin stx), invasion genes (virB, ipaABCD, ippI)[5] |

TABLE 8-continued

| Waterborne Fecal-Oral Route Pathogens | | | |
|---|---|---|---|
| Type | Illness | Detection Issues | Molecular Targets |
| Enterotoxigenic E. coli (ETEC) | Diarrhea | | (indirect reference) List of ninety one virulence genes including those encoding toxins, adhesion factors, secretion systems, capsule antigens, somatic antigens, flagellar antigens, invasins, autotransporters and aerobactin systems studied for creation of a E. coli Pathotype DNA microarray.[6] Review article, Diarrheagenic E. coli.[7] |
| Enterococcus | Diarrhea | | PCR assay for detection of Enterococci at genus level by targeting tuf gene.[8] Multiplex PCR for detection of asa1, gelE, cylA, esp and hyl genes in Enterococci.[9] |
| Vibrio cholerae | Cholera | | (indirect reference) Expression of toxT controls the expression of several virulence factors.[10] Review article, Epidemiology, Genetics and Ecology of Toxigenic Vibrio cholerae.[11] Genotypes associated with virulence in environmental isolates of vibrio cholerae.[12] |
| Staphlyococcus aureus | | | Single-reaction multiplex PCR toxin typing assay for enterotoxin genes A-E.[13] |
| Campylobacter jejuni | Gastroenteritis | | Random amplified polymorphic DNA (RAPD) identifies invasion-associated marker (IAM). Differentiation possible using RAPD and PCR using primers targeting iam locus.[14] |
| Viruses | | | |
| Hepatitis A | Hepatitis | | Member of Picornaviridae family |
| Norwalk like agents | Gastroenteritis | | Caliciviruses |
| Virus-like 27 nm particles | Gasteroenteritis | | |
| Rotavirus | Gastroenteritis and polio | | Reoviridae family |

TABLE 8-continued

Waterborne Fecal-Oral Route Pathogens

| Type | Illness | Detection Issues | Molecular Targets |
|---|---|---|---|
| Protozoa | | | |
| *Cryptosporidium parvum* | Cryptosporidiosis | | *Cryptosporidium* spp. |
| *Giardia lablia* | Giardisis | | ELISA available, otherwise microscopic exam |
| *Entamoeba histolytica* | Amoebic dystentery | | |

[1] Evaluation of IS200-PCR and Comparison with Other Molecular Markers to Trace *Salmonella enterica* subsp. *enterica* Serotype *Typhimurium* Bovine Isolates from Farm to Meat. Millemann Y, Gaubert S, Remy D, Colmin C. *J Clin Microbiol*. 2000 Jun; 38(6): 2204-2209.
[2] Differential Patterns of Acquired Virulence Genes Distinguish *Salmonella* Strains. Conner CP, Heithoff DM, Julio SM, Sinsheimer RL, Mahan MJ. *Proc Natl Acad Sci U S A*. 1998 Apr 14; 95(8): 4641-4645.
[3] Characterization of *Salmonella enterica* Subspecies I Genovars by Use of Microarrays. Porwollik S, Boyd E F, Choy C, Cheng P, Florea L, Proctor E, McClelland M. *J Bacteriol*. 2004 Sep; 186(17): 5883-5898.
[4] Molecular Basis of the Interaction of *Salmonella* with the Intestinal Mucosa. Darwin KH, Miller VL. *Clin Microbiol Rev*. 1999 Jul; 12(3): 405-428.
[5] Genetic basis of Virulence in *Shigella* Species. Hale T L. Microbiol Rev. 1991 Jun; 55(2): 206-224.
[6] Rapid Identification of *Escherichia coli* Pathotypes by Virulence Gene Detection with DNA Microarrays. Bekal S, Brousseau R, Masson L, Prefontaine G, Fairbrother J, Harel J. *J Clin Microbiol*. 2003 May; 41(5): 2113-2125.
[7] Diarrheagenic *Escherichia coli*. Nataro J P, Kaper J B. *Clin Microbiol Rev*. 1998 Jan; 11(1): 142-201.
[8] Development of a PCR Assay for Rapid Detection of *Enterococci*. Ke D, Picard F J, Martineau F, Ménard C, Roy P H, Ouellette M, Bergeron M G. *J Clin Microbiol*. 1999 Nov; 37(11): 3497-3503.
[9] Development of a Multiplex PCR for the Detection of asa1, gelE, cylA, esp, and hyl Genes in *Enterococci* and Survey for Virulence Determinants Among European Hospital Isolates of *Enterococcus faecium*. Vankerckhoven V, Van Autgaerden T, Vael C, Lammens C, Chapelle S, Rossi R, Jabes D, Goossens H. *J Clin Microbiol*. 2004 Oct; 42(10): 4473-4479.
[10] pepA, a Gene Mediating pH Regulation of Virulence Genes in *Vibrio cholerae*. Behari J, Stagon L, Calderwood S B. *J Bacteriol*. 2001 Jan; 183(1): 178-188.
[11] Epidemiology, Genetics, and Ecology of Toxigenic *Vibrio cholerae*. Faruque S M, Albert M J, Mekalanos J J, *Microbiol Mol Biol Rev*. 1998 Dec; 62(4): 1301-1314.
[12] Genotypes Associated with Virulence in Environmental Isolates of *Vibrio cholerae*. Rivera I N, Chun J, Huq A, Sack R B, Colwell R R. *Appl Environ Microbiol*. 2001 Jun; 67(6): 2421-2429.
[13] Development of a Single-Reaction Multiplex PCR Toxin Typing Assay for *Staphylococcus aureus* Strains. Sharma N K, Rees C E, Dodd C E. *Appl Environ Microbiol*. 2000 Apr; 66(4): 1347-1353.
[14] Molecular Characterization of Invasive and Noninvasive *Campylobacter jejuni* and *Campylobacter coli* Isolates. Carvalho A C, Ruiz-Palacios G M, Ramos-Cervantes P, Cervantes L E, Jiang X, Pickering L K. *J Clin Microbiol*. 2001 Apr; 39(4): 1353-1359.

Fermentation

Fermentation.

During fermentation processes microbial growth and metabolism leads to the production of a wide range of metabolites. These metabolites include alcohols, proteins, lipids, vitamins, antimicrobial compounds (e.g., bacteriocins and lysozyme); texture-forming agents (e.g., xanthan gum); amino acids; organic acids (e.g. citric acid, lactic acid), and flavor compounds (e.g., esters and aldehydes). Many of these microbial metabolites are commercially valuable (e.g., flavor compounds, amino acids, organic acids, enzymes, xanthan gums, alcohol etc.) and are produced through industrial scale fermentation processes.

The microorganisms which are used in industrial scale fermentation processes are selected based on their having desirable attributes. Such attributes include their ability to enhance sensory qualities (flavor, aroma, visual appearance, texture and consistency), induce resistance to viruses (bacteriophage) in the case of dairy fermentations, the ability to produce antimicrobial compounds (e.g. bacteriocins, hydrogen peroxide) for the inhibition of undesirable microorganisms, and the ability to degrade or inactivate natural toxins in food substrates such as cyanogenic glucosides in cassava, mycotoxins in cereal fermentations and anti-nutritional factors (e.g. phytates).

It is therefore desirable to prepare a 'Fermentation Performance Index' based on the presence or absence of specific microbial behavioral characteristics. Such an index can be prepared by an appropriate combination (in the Sanitation Index type approach) of presence/absence signals of the following microbial behavioral characteristic markers:

Protosymbiosis between *Streptococcus thermophilus* and *Lactobacillus delbrueckii* subsp. *bulgaricus* (genus specific marker for both species to show presence of both, and thus a useful yogurt culture)[1]

Gene specific markers for lactic acid, acetylaldehyde, acetic acid, and diacetyl production in *Lactobacillii* (allows detection of 'start culture' flavor behavior upon inoculation);

[1] Probiotic Bacteria in Fermented Foods: Product Characteristics and Starter Organisms Heller, K., *American Journal of Clinical Nutrition*. February 2001; 73(2): 374S-379S.

These, and many other applications of the inventive microbial monitoring methods will be recognized by those of skill in the art, and are encompassed within the present invention.

The invention claimed is:

1. A method for process control with respect to a target microbe, comprising:
   a) obtaining during each of a plurality of time periods, at least one test sample from a process or system receptive to a plurality of genetically distinct microbes;
   b) testing for presence or absence for each of a plurality of suitable markers of at least one target microbe to provide a set of test results for each sample, wherein at least one of the markers also detects at least one index microbe, other than the target microbe, potentially present in the sample and genetically distinct from the target microbe but is positive for a subset of the plurality of tested markers;
   c) calculating for each set of test results, at least one mathematical index value relating the number of markers for which positive results are obtained to the total number of tested markers, wherein the index value is predictive of the presence or absence of the target microbe; and initiating remedial action when the index value achieves a threshold value indicative of process failure and presence of the target microbe, wherein a method for process control with respect to the target microbe is afforded.

2. The method of claim 1, wherein the index microbe is a microbe that is genetically distinct from the at least one target microbe, but is otherwise correlatable with the target microbe by virtue of at least one common property selected from the group consisting of: coordinate source association; coordinate growth condition response; indicator organism relationship; same family taxon; same genus taxon; same species taxon; same biotype; same serotype; same virulence group; common functional genes; common virulence factors; common enzymes and enzymatic pathway(s); common engineered genes or traits; common metabolites or by-products; coordinate sensitivity to antimicrobial agents or conditions, and same strain attribution.

3. The method of claim 1, wherein the samples are enriched prior to testing in b).

4. The method of claim 1, wherein the at least one mathematical index value determined in c) allows for normalizing the number of observed marker presence events over the number of samples taken.

5. The method of claim 1, wherein determining the at least one mathematical index value in c) further comprises weighting, for purposes of calculating the index value, the value of the presence of at least one of the markers relative to another.

6. The method of claim 5, wherein the weighting is based on at least one common property between target and index microbes, wherein the index microbe is a microbe that is genetically distinct from the at least one target microbe, but is otherwise correlatable with the target microbe by virtue of at least one common property selected from the group consisting of: coordinate source association; coordinate growth condition response; indicator organism relationship; same family taxon; same genus taxon; same species taxon; same biotype; same serotype; same virulence group; common functional genes; common virulence factors; common enzymes and enzymatic pathway(s); common engineered genes or traits; common metabolites or by-products; coordinate sensitivity to antimicrobial agents or conditions, and same strain attribution.

7. The method of claim 1, wherein the at least one target microbe is considered present when a specific marker profile is determined to be present.

8. The method of claim 1, wherein the threshold mathematical index value is an upper confidence limit, that is proportional to the standard deviation of the index values over an investigated time range.

9. The method of claim 1, wherein the markers are selected from the group consisting of genetic markers, antigenic markers, metabolite and metabolite by-product markers, and combinations thereof.

10. The method of claim 1, wherein the number of markers tested is at least 5.

11. The method of claim 1, wherein the time periods are separated by a period selected from the group consisting of seconds, minutes, hours, days, weeks, months, years and combinations thereof.

12. The method of claim 1, wherein the at least one target microbe is selected from the group consisting of a pathogens, spoilage organisms, beneficial organisms, bioremedial organisms, indicator organisms, fermentation-related organisms, and combinations thereof.

13. The method of claim 1, wherein the tests are selected from the group consisting of immunoassays, ELISA assays, antigen-antibody based detection methods, ligand-antigen detection methods, nucleic acid amplification-based assays, PCR, multiplex PCR, nucleic acid hybridization-based assays, bio-sensor assays, immunostaining-microscopy-based assays, nucleic acid-array-based assays, DNA chip-based assays, dot blots, multi- and single-target lateral flow devices, bacteriophage-detection-based assays, microbiology-based assays, and chemical and biochemical assays for detection of compounds, microbial byproducts, metabolites, organic and inorganic molecules associated with the at least one target microbe.

14. The method of claim 1, wherein the test sample is a composite sample comprised of a plurality of samples collected from different sources or locations within the process or system.

15. The method of claim 1, wherein the at least one threshold index value corresponds to a particular process interval selected from the group consisting of daily, weekly, monthly, seasonal, and process phase based intervals, and is predictive of a status of the process or system.

16. The method of claim 9, wherein the markers are selected from the group consisting of DNA markers, virulence factor genes, virulence factors or putative virulence factors, toxins, enzymes, proteins, macromolecules, metabolic byproducts, surface antigens, adhesion proteins, ribosomal gene markers, and combinations thereof.

17. The method of claim 10, wherein at least one marker comprises an antigen of a surface antigen protein of the target microbe, and at least 4 markers correspond to genetic markers of the target organism.

18. The method of claim 12, wherein the pathogen is characterized by at least one property selected from the group consisting of foodborne, waterborne, airborne, bloodborne, sexually transmitted, vectorborne, and zoonotic organism.

19. The method of claim 12, wherein the pathogen is selected from the group consisting of bacterial, viral, fungal and parasitic microorganisms, and by-products of the preceding.

20. The method of claim 12, wherein the pathogen is selected from the group consisting of bacterial, viral parasitic and fungal.

21. The method of claim 20, wherein the pathogenic organism is *E. coli* O157:H7.

* * * * *